United States Patent
Periana et al.

(10) Patent No.: US 11,078,136 B2
(45) Date of Patent: Aug. 3, 2021

(54) OXIDATION OF ALKANE TO ALKENE

(71) Applicants: The Scripps Research Institute, La Jolla, CA (US); Hyconix, Inc., Chicago, IL (US)

(72) Inventors: Roy A. Periana, Jupiter, FL (US); Brian G. Hashiguchi, Naperville, IL (US); Michael M. Konnick, Aurora, IL (US)

(73) Assignees: The Scripps Research Institute, La Jolla, CA (US); Hyconix, Inc., Chicago, IL (US)

(*) Notice: Subject to any disclaimer, the term of this patent is extended or adjusted under 35 U.S.C. 154(b) by 10 days.

(21) Appl. No.: 16/616,615

(22) PCT Filed: May 25, 2018

(86) PCT No.: PCT/US2018/034706
§ 371 (c)(1),
(2) Date: Nov. 25, 2019

(87) PCT Pub. No.: WO2018/218176
PCT Pub. Date: Nov. 29, 2018

(65) Prior Publication Data
US 2020/0095179 A1   Mar. 26, 2020

Related U.S. Application Data

(60) Provisional application No. 62/654,119, filed on Apr. 6, 2018, provisional application No. 62/654,133, filed
(Continued)

(51) Int. Cl.
*C07C 5/50*  (2006.01)
*C07C 29/132*  (2006.01)
(Continued)

(52) U.S. Cl.
CPC .............. *C07C 5/50* (2013.01); *C07C 29/132* (2013.01); *C07C 29/50* (2013.01); *C07C 31/202* (2013.01);
(Continued)

(58) Field of Classification Search
CPC .... C07C 5/42; C07C 5/44; C07C 5/46; C07C 5/48; C07C 5/5054; C07C 5/56;
(Continued)

(56) References Cited

U.S. PATENT DOCUMENTS 4,112,241 A   9/1978   Okano et al.
4,508,653 A   4/1985   Goel
(Continued)

FOREIGN PATENT DOCUMENTS

DE     108969 A1    10/1974
RU    2139846 C1   10/1999
(Continued)

OTHER PUBLICATIONS

Russian Patent Office, Official Action and Search Report in Russian Patent Application No. 2019143406 (dated Mar. 25, 2020).
(Continued)

*Primary Examiner* — Youngsul Jeong
*Assistant Examiner* — Jason Y Chong
(74) *Attorney, Agent, or Firm* — Leydig, Voit & Mayer, Ltd.

(57) ABSTRACT

Provided is a process for converting an alkane to an alkene. The process comprises (a) contacting the alkane and either (i) an oxidizing electrophile comprising a main group element in oxidized form, or (ii) an oxidant and a reduced form of the oxidizing electrophile, in a liquid medium comprising an oxygen acid and optionally one or more additives selected from a non-oxidizable liquid, a salt additive, a Lewis acid, and water, to provide an oxidized intermediate
(Continued)

CH Activation

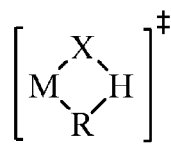

TS1

MR Functionalization

TS2

Net:

and a reduced form of the oxidizing electrophile; (b) optionally separating the oxidized intermediate and the reduced form of the oxidizing electrophile; and (c) performing an elimination reaction on the oxidized intermediate to provide the alkene and the oxygen acid.

23 Claims, 5 Drawing Sheets

Related U.S. Application Data on Apr. 6, 2018, provisional application No. 62/511,173, filed on May 25, 2017.

(51) Int. Cl.
  *C07C 29/50* (2006.01)
  *C07C 31/20* (2006.01)

(52) U.S. Cl.
  CPC ........ *C07C 31/205* (2013.01); *C07C 2523/18* (2013.01); *C07C 2531/04* (2013.01)

(58) Field of Classification Search
  CPC ....... C07C 29/03; C07C 29/09; C07C 29/132; C07C 29/48; C07C 29/50; C07C 2523/18; C07C 2531/04; C07C 1/20; C07C 27/16
  See application file for complete search history.

(56) References Cited

U.S. PATENT DOCUMENTS

| | | | |
|---|---|---|---|
| 5,686,369 A | 11/1997 | Chen et al. | |
| 2016/0002139 A1* | 1/2016 | Periana | C07C 67/035 560/131 |

FOREIGN PATENT DOCUMENTS

| | | |
|---|---|---|
| SU | 722890 A1 | 3/1980 |
| WO | WO 2014/130987 A1 | 8/2014 |
| WO | WO 2015/021126 A1 | 2/2015 |

OTHER PUBLICATIONS

Hashiguchi et al., Designing Catalysts for Functionalization of Unactivated C—H Bonds Based on the CH Activation Reaction, *Accounts of Chemical Rese*, 45(6): 885-898 (Jun. 19, 2012).

European Patent Office, International Search Report and the Written Opinion in International Application No. PCT/US2018/034706 (dated Jul. 23, 2018).

European Patent Office, International Search Report and the Written Opinion in International Application No. PCT/US2018/034698 (dated Sep. 6, 2018).

European Patent Office, International Search Report and the Written Opinion in International Application No. PCT/US2018/034717 (dated Oct. 24, 2018).

* cited by examiner

CH Activation

MR Functionalization

TS1           TS2

$MX_2 + RH \longrightarrow MX\text{-}R + HX \longrightarrow M + R\text{-}X + HX$ $M + 2\,HX + Ox \longrightarrow MX_2 + H_2Ox$

---

Net:  $R\text{-}H + HX + Ox \longrightarrow RX + H_2Ox$

M = As, Sb, or Bi, n = 3, z = 4
M = Te or Se, n = 4, z = 5
M = Sn, n = 2, z = 3

| Entry | Substrate | Oxidant | [Oxidant] (mM) | Liquid Species | Additive | [Additive] (mM) | Temp (°C) | Time (h) |
|---|---|---|---|---|---|---|---|---|
| 1 | Propane | Sb(TFA)$_3$/H$_2$O$_2$ | 100 | TFAH | TFA$_2$O/NaTFA | 637/100 | 180 | 3 |
| 2 | Propane | Na[Sb(OH)$_6$] | 100 | TFAH | TFA$_2$O | 637 | 180 | 17 |
| 3 | Propane | Sb(TFA)$_3$/H$_2$O$_2$ | 300 | TFAH | TFA$_2$O/C$_6$F$_5$CO$_2$H | 707/1000 | 150 | 1 |
| 4 | Propane | Sb(TFA)$_3$/H$_2$O$_2$ | 100 | TFAH | TFA$_2$O/Pyrazine | 500/100 | 150 | 3 |
| 5 | Propane | Sb(TFA)$_3$/H$_2$O$_2$ | 100 | Et(TFA)$_2$/TFAH | TFA$_2$O/C$_6$F$_5$CO$_2$H | 500/100 | 150 | 3 |
| 6 | Propane | Pb(OAc)$_4$ | 100 | HOAc | N/A | N/A | 130 | 3 |
| 7 | Propane | Pb(OAc)$_4$ | 100 | HOAc | NaOAc | 300 | 130 | 3 |
| 8 | Propane | Pb(OAc)$_4$ | 100 | HOAc | H$_2$O | 1000 | 130 | 3 |
| 9 | Propane | Pb(OAc)$_4$ | 100 | HOAc | H$_2$SO$_4$ | 275 | 130 | 3 |
| 10 | Propane | Pb(TFA)$_4$ | 100 | TFAH | N/A | N/A | 130 | 3 |
| 11 | Propane | Pb(TFA)$_4$ | 100 | TFAH | NaTFA | 300 | 130 | 3 |
| 12 | Propane | Pb(TFA)$_4$ | 100 | TFAH | H$_2$O | 1000 | 130 | 3 |
| 13 | Propane | I(TFA)$_3$ | 300 | TFAH | N/A | N/A | 180 | 2 |
| 14 | Propane | C$_6$F$_5$I(TFA)$_2$ | 780 | TFAH | TFA$_2$O | 100 | 140 | 1 |
| 15 | Propane | C$_6$F$_5$I(TFA)$_2$ | 100 | AcOH | Ac$_2$O | 100 | 150 | 3 |
| 16 | Propane | C$_6$F$_5$I(TFA)$_2$ | 100 | TFAH | N/A | N/A | 140 | 1 |
| 17 | Propane | C$_6$H$_5$I(CO$_2$)$_2$ | 100 | TFAH | N/A | N/A | 170 | 3 |
| 18 | Ethane | C$_6$F$_5$I(TFA)$_2$ | 780 | TFAH | TFA$_2$O | 100 | 140 | 1 |
| 19 | Ethane | Sb(TFA)$_3$/H$_2$O$_2$ | 100 | TFAH | TFA$_2$O/C$_6$F$_5$CO$_2$H | 500/100 | 150 | 3 |
| 20 | Ethane | [Sb(OMe)$_5$]$_2$ | 50 | TFAH | TFA$_2$O | 2360 | 150 | 4 |
| 21 | Ethane | Sb(TFA)$_3$/H$_2$O$_2$ | 50 | TFAH | TFA$_2$O | 687 | 150 | 4 |

FIG. 6A

| Entry | Major Product | % Major Product | Minor Product | % Minor Product | Total (% Yield) |
|---|---|---|---|---|---|
| 1 | iPrTFA | 4 | | 0 | 4 |
| 2 | iPrTFA | 4 | | 0 | 4 |
| 3 | 1,2-Pr(TFA)$_2$ | 30 | iPrTFA | 12 | 42 |
| 4 | iPrTFA | 4 | | 0 | 4 |
| 5 | iPrTFA | 8 | 1,2-Pr(TFA)$_2$ | 2 | 10 |
| 6 | iPrOAc | 25 | 1,2-Pr(OAc)$_2$ | 7 | 32 |
| 7 | iPrOAc | 35 | 1,2-Pr(OAc)$_2$ | 20 | 55 |
| 8 | iPrOAc | 37 | 1,2-Pr(OAc)$_2$ | 22 | 59 |
| 9 | iPrOAc | 10 | 1,2-Pr(OAc)$_2$ | 6 | 16 |
| 10 | iPrTFA | 55 | 1,2-Pr(TFA)$_2$ | 36 | 91 |
| 11 | iPrTFA | 53 | 1,2-Pr(TFA)$_2$ | 40 | 93 |
| 12 | iPrTFA | 54 | 1,2-Pr(TFA)$_2$ | 34 | 88 |
| 13 | iPrTFA | 40 | 1,2-Pr(TFA)$_2$ | 2 | 42 |
| 14 | 1,2-Pr(TFA)$_2$ | 48 | iPrTFA | 26 | 74 |
| 15 | 1,2-Pr(X)$_2$ X = OAc or TFA | 53 | iPr(X) X = OAc or TFA | 34 | 87 |
| 16 | iPrTFA | 35 | 1,2-Pr(TFA)$_2$ | 12 | 47 |
| 17 | iPrTFA | 50 | nPrTFA | 3 | 53 |
| 18 | EtTFA | 67 | Et(TFA)$_2$ | 13 | 80 |
| 19 | EtTFA | 8 | Et(TFA)$_2$ | 2 | 10 |
| 20 | EtTFA | 14 | Et(TFA)$_2$ | 9 | 32 |
| 21 | EtTFA | 14 | Et(TFA)$_2$ | 8 | 30 |

FIG. 6B

OXIDATION OF ALKANE TO ALKENE

CROSS-REFERENCE TO RELATED APPLICATIONS

This patent application is a U.S. national phase of International Patent Application No. PCT/US2018/034706, filed May 25, 2018, which claims the benefit of U.S. Provisional Patent Application 62/654,133, filed Apr. 6, 2018, U.S. Provisional Patent Application 62/654,119, filed Apr. 6, 2018, and U.S. Provisional Patent Application 62/511,173, filed May 25, 2017, the disclosures of which are incorporated herein by reference in their entireties for all purposes.

BACKGROUND OF THE INVENTION

Alkenes are the largest volume organic commodity chemicals produced worldwide, and they play a role in producing other large commodity chemicals. However, efficient and low-cost techniques for using relatively unreactive small molecules, such as alkanes, to produce alkenes are currently underdeveloped in the chemical industry.

The chemical industry generally produces commodity scale alkenes via a variant of cracking technology. For example, over 90% of currently produced ethylene is derived from the steam cracking of naphtha, ethane, and/or propane, as shown in equation 1:

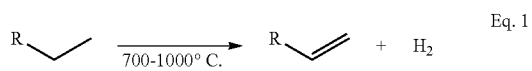

Eq. 1

This reaction takes place at high temperatures (i.e., about 700° C. to about 1000° C.) and requires millisecond residence times; moreover, product selectivity drastically decreases if the effluent is not quenched immediately. Additionally, longer alkenes, such as 1-octene, are formed through a completely different process, such as the oligomerization of ethylene. This technique, however, is costly and leaves a large carbon footprint.

Recently, new techniques have been emerging that convert light alkanes (e.g., ethane and propane) and oxygen to alkenes. These techniques use the oxidative dehydrogenation reaction shown in equation 2:

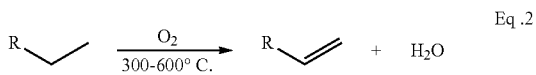

Eq. 2

This oxidative dehydrogenation reaction operates at lower temperatures (i.e., about 300° C. to about 600° C.) than the reaction used in cracking technologies; however, it is often plagued by low conversion, and it usually results in overoxidation to $CO_2$ and coke which deactivates the heterogeneous catalyst. This reaction can also result in low product selectivity.

Thus, the current techniques for alkene production either require the use of high temperatures or suffer from low conversion and/or low product selectivity. Therefore, a need exists in the chemical industry for a low temperature alternative that results in high conversion and/or high selectivity of a desired alkene product. Moreover, a need exists for a cost-effective, alkene production process that results in a reduced carbon footprint.

BRIEF SUMMARY OF THE INVENTION

The invention provides a process for converting an alkane to an alkene comprising, consisting essentially of, or consisting of: (a) contacting the alkane and either (i) an oxidizing electrophile comprising a main group element in oxidized form, or (ii) an oxidant and a reduced form of the oxidizing electrophile, in a liquid medium comprising an oxygen acid and optionally one or more additives selected from a non-oxidizable liquid, a salt additive, a Lewis acid, and water, to provide an oxidized intermediate and a reduced form of the oxidizing electrophile; (b) optionally separating the oxidized intermediate and the reduced form of the oxidizing electrophile; and (c) performing an elimination reaction on the oxidized intermediate to provide the alkene and the oxygen acid.

BRIEF DESCRIPTION OF THE DRAWING

FIG. 6A is a table of exemplary reaction conditions for the procedure outlined in Example 4. FIG. 6B is a table of exemplary results for the procedure outlined in Example 4.

DETAILED DESCRIPTION OF THE INVENTION

The invention provides a process for converting an alkane to an alkene comprising, consisting essentially of, or consisting of: (a) contacting the alkane and either (i) an oxidizing electrophile comprising a main group element in oxidized form, or (ii) an oxidant and a reduced form of the oxidizing electrophile, in a liquid medium comprising an oxygen acid and optionally one or more additives selected from a non-oxidizable liquid, a salt additive, a Lewis acid, and water, to provide an oxidized intermediate and a reduced form of the oxidizing electrophile; (b) optionally separating the oxidized intermediate and the reduced form of the oxidizing electrophile; and (c) performing an elimination reaction on the oxidized intermediate to provide the alkene and the oxygen acid.

The process converts an alkane to an alkene. The effectiveness of the process, described herein, is best viewed in terms of the oxidizing electrophile's ability to react selectively with a functionalized or unfunctionalized alkane to form an oxidized intermediate (e.g., R—OY). The oxidized intermediate can optionally then be separated from a reduced form of the oxidizing electrophile, before an elimination reaction is performed on the oxidized intermediate to provide the alkene. Products generated from the direct oxidation of an alkane are less reactive than the corresponding alkane; moreover, the groups (e.g., —OY) in the oxidized intermediate are more electron-withdrawing than the hydrogen in the corresponding C—H bond of a functionalized or unfunctionalized alkane (i.e., R—H). This oxidative process is advantageous because it typically generates products with high selectivity and high alkane conversion.

Alkanes typically require harsh reaction conditions (e.g., free radical-based chemistry) to undergo chemical transformations, and traditional techniques tend to result in complex product mixtures that include over-oxidized products. In contrast to conventional techniques, the process, described herein, does not utilize harsh reaction conditions to form the alkene. More particularly, the process does not form the alkene by a free radical mechanism. Without wishing to be bound by any theory, it is believed that the mechanism by which the process converts an alkane to an oxidized intermediate, which subsequently generates the corresponding alkene, occurs through an electrophilic C—H activation ("CHA") reaction.

Figure 1:
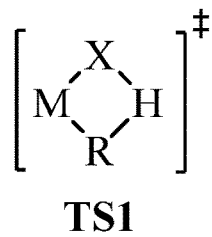
FIG. 1 illustrates the conversion of R—H to R—X via C—H activation and M-R functionalization.
Figure 1:
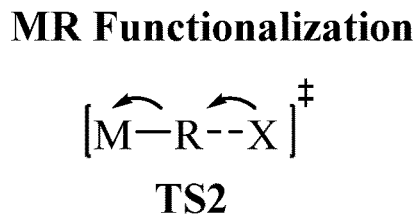

An important emerging approach to the direct oxidation of C—H bonds of alkanes to C—X bonds (where X is a heteroatom containing group) is based on the electrophilic C—H activation reaction shown in FIG. 1. This reaction involves the species $MX_2$, which reacts directly with R—H (i.e., a C—H bond of an alkane) to generate H—X and MX—R intermediates. A key advantage of the C-H activation reaction is that cleavage of the R—H bond proceeds by a concerted process involving a single transition state (TS1), where, as the R—H bond is cleaved, the new M-R and H—X bonds are created. Three important advantages of this concerted cleavage are (i) no reactive species (e.g., free radicals, carbocations, or carbanions) are generated that can lead to unselective reactions, (ii) as the energy input required to cleave the R—H bond is moderated by the energy released in the formation of the new M-R and H—X bonds, these reactions can be quite facile, and (iii) the properties of M and X can be adjusted to ensure that the product, R—X, is less reactive than the substrate, R—H. Using $MX_2$ species that can subsequently undergo redox reactions allows the C—H activation to be coupled to an M-R functionalization reaction. The resulting M-R functionalization reaction proceeds by a concerted process involving a single transition state (TS2) and can selectively generate functionalized products (R—X) and reduced species (M). As shown in FIG. 1, reoxidation of M with an oxidant (Ox) can allow an overall reaction of R—H with Ox to generate R—X without consumption of $MX_2$.

Previously, it has been shown that an electrophilic oxidant of the formula $M(OY)_2$ is capable of facilitating the direct oxidation of an alkane to form the corresponding alcohol, via an electrophilic C—H activation ("CHA") reaction. It is particularly effective when carried out in the corresponding acid solvent, HOY (e.g., $H_2SO_4$, $HSO_3CF_3$, $HCO_2CF_3$, and $HSO_3CH_3$). It has not been shown, however, that combining a selective C—H-functionalization reaction with an elimination reaction of an oxidized intermediate efficiently produces an alkene from an alkane. The present invention provides a novel process, which generates alkenes at lower costs and with reduced emissions relative to current technologies.

The process comprises converting an alkane to an alkene. As used herein, the term "alkane" refers to any organic molecule comprising at least two adjacent $sp^3$ hybridized carbon atoms, (i.e., the alkane-containing portion; also considered an alkyl-containing compound). The adjacent $sp^3$ hybridized carbon atoms can be methine, methylene, methyl, or a combination thereof. The alkane can be substituted, unsubstituted, branched, straight-chained, cyclic, or a combination thereof, and can be fully saturated or includes portions that are unsaturated or aromatic, provided that the alkane has at least one $sp^3$ hybridized carbon atom with at least one C—H bond (e.g., 1, 2, or 3) adjacent to a second $sp^3$ hybridized carbon atom with at least one C—H bond (e.g., 1, 2, or 3). For example, the alkane can comprise one or more olefinic moeities such that when the alkane is converted to an alkene, the alkene is a diene, triene, etc. In some embodiments, the alkane is a $C_2$-$C_{20}$ alkane, a $C_2$-$C_{20}$ heteroalkane, $C_3$-$C_{20}$ cycloalkane, $C_3$-$C_{20}$ heterocycloalkane, arylalkane, heteroarylalkane, or a combination thereof. In further embodiments, the alkane is ethane, propane, butane, or a mixture thereof.

The term "$C_2$-$C_{20}$ alkane" refers to a substituted or unsubstituted $C_2$-$C_{20}$ alkyl carbon chain from 2 to 20 (i.e., 2, 3, 4, 5, 6, 7, 8, 9, 10, 11, 12, 13, 14, 15, 16, 17, 18, 19, or 20) carbons in length. In some embodiments, the $C_2$-$C_{20}$ alkane can be saturated, unsaturated, branched, straight-chained, cyclic, or a combination thereof, so long as the $C_2$-$C_{20}$ alkane has at least two adjacent $sp^3$ hybridized methine, methylene, and/or methyl groups. An exemplary, but non-limiting list of $C_2$-$C_{20}$ alkanes includes ethane, propane, n-butane, 1-butene, isobutane, 1-pentene, pentane, isopentane, neopentane, and structural isomers of hexane, heptane, octane, nonane, decane, or a combination thereof.

As used herein, "$C_2$-$C_{20}$ heteroalkane" refers to a substituted or unsubstituted $C_2$-$C_{20}$ alkane which contains at least 1 heteroatom (e.g., O, S, N, and/or P) in the core of the molecule (i.e., any part of the molecule except for the alkane-containing portion). Accordingly, at least 1 heteroatom can be a pendant substituent or part of a carbon chain. In certain instances, the $C_2$-$C_{20}$ heteroalkane has at least 2 heteroatoms in the core of the molecule (e.g., at least 3, 4, 5, or 6 heteroatoms in the core of the molecule). In some embodiments, the $C_2$-$C_{20}$ heteroalkane compound comprises a moiety selected from an ether, an ester, a carbonate, an amide, an amine, a carbamate, a thioether, a thioester, a phosphate, a heterocycloalkane, a haloalkane, an acetyl, an alcohol, a ketone, an aldehyde, a carboxylate, a carboxylic acid, a hemiacetal, an acetal, a ketal, an imine, and imide, a thiol, a disulfide, a sulfoxide, a thioketone, or a combination thereof. The heteroalkane can be substituted, unsubstituted, branched, straight-chained, cyclic, or a combination thereof.

The term "$C_3$-$C_{20}$ cycloalkane," as used herein, refers to a substituted or unsubstituted $C_3$-$C_{20}$ alkane comprising a cyclic alkane moiety containing from, for example, 3 to 6 carbon atoms or from 5 to 6 carbon atoms. In some embodiments, the $C_3$-$C_{20}$ cycloalkane is cyclopropane, cyclobutane, cyclopentane, or cyclohexane. In some embodiments, the $C_3$-$C_{20}$ cycloalkane can be a cycloalkane, as long as the cycloalkane comprises an alkane-containing portion. The term "cycloalkene" refers to a cycloalkane, as described herein, with at least one C—C double bond in the ring. For example, the cycloalkene can be cyclopentene or cyclohexene. In some embodiments, the $C_3$-$C_{20}$ cycloalkane can be converted to an arene. The term "arene" refers to an unsubstituted or substituted aromatic carbocyclic moiety that is planar and comprises $4n+2\pi$ electrons, according to Hückel's Rule, wherein n=1, 2, or 3, as commonly understood in the art. The term "arene" includes monocyclic and polycyclic aromatics and generally contains from, for example, 6 to 30 carbon atoms (e.g., from 6 to 18 carbons, from 6 to 14 carbons, or from 6 to 10 carbons).

The term "$C_3$-$C_{20}$ heterocycloalkane," as used herein, refers to a $C_3$-$C_{20}$ alkane comprising a cyclic alkane moiety containing from, for example, 3 to 6 carbon atoms or from 5 to 6 carbon atoms which contains at least 1 heteroatom (e.g., O, S, N, and/or P) in the core of the molecule (i.e., any part of the molecule except for the alkane-containing portion). Accordingly, at least 1 heteroatom can be a pendant substituent or encompassed in a cyclic chain. In certain instances, the $C_3$-$C_{20}$ heterocycloalkane has at least 2 heteroatoms in the core of the molecule (e.g., at least 3, 4, 5, or 6 heteroatoms in the core of the molecule). In some embodiments, the $C_3$-$C_{20}$ heterocycloalkane compound comprises a moiety selected from an ether, an ester, a carbonate, an amide, an amine, a carbamate, a thioether, a thioester, a phosphate, a haloalkane, an acetyl, an alcohol, a ketone, an aldehyde, a carboxylate, a carboxylic acid, a hemiacetal, an acetal, a ketal, an imine, and imide, a thiol, a disulfide, a sulfoxide, a thioketone, or a combination thereof. An exemplary, but non-limiting list of $C_3$-$C_{20}$ heterocycloalkanes includes tetrahydrofuran, piperazine, morpholine, cyclohexanone, and 2-cyclohexylethanol.

As used herein, "arylalkane" refers to a $C_6$-$C_{20}$ alkane comprising a substituted or unsubstituted, monocyclic or polycyclic aromatic substrate (e.g., phenyl, xylenyl, naphthyl, biphenyl, anthracyl, or a combination thereof). An exemplary arylalkane is ethylbenzene.

As used herein, "heteroarylalkane" refers to a $C_6$-$C_{20}$ arylalkane which contains at least 1 heteroatom (e.g., O, S, N, and/or P) in the core of the molecule (i.e., any part of the molecule except for the alkane-containing portion). Accordingly, at least 1 heteroatom can be a pendant substituent or encompassed in a monocyclic or polycyclic heteroaromatic substituent. In certain instances, the heteroarylalkane has at least 2 heteroatoms in the core of the molecule (e.g., at least 3, 4, 5, or 6 heteroatoms in the core of the molecule).

In some embodiments, the heteroarylalkane comprises a monocyclic or polycylic heteroaromatic substrate. The term "heteroaromatic substrate" refers to an aromatic compound which has at least one heteroatom (O, S, or N) in at least one of the rings. In certain embodiments, the heteroaromatic substrate is polycyclic and has 2, 3, or 4 aromatic rings. Each ring of the heteroaromatic substrate containing a heteroatom can contain one or two oxygen and/or sulfur atoms and/or from one to four nitrogen atoms provided that the total number of heteroatoms in each ring is four or less and each ring has at least one carbon atom. The fused rings completing the polycyclic groups can contain only carbon atoms and can be saturated, partially saturated, or unsaturated. The nitrogen and sulfur atoms can optionally be oxidized, and the nitrogen atoms can optionally be quaternized. Heteroaromatic substrates that are polycyclic must include at least one fully aromatic ring but the other fused ring or rings can be aromatic or non-aromatic. In some embodiments, the heteroaromatic substrate is pyrrolyl, isoindolyl, indolizinyl, indolyl, furanyl, benzofuranyl, benzothiophenyl, thiophenyl, pyridyl, acridinyl, naphthyridinyl, quinolinyl, isoquinolinyl, isoxazolyl, oxazolyl, benzoxazolyl, isothiazolyl, thiazolyl, benzthiazolyl, imidazolyl, thiadiazolyl, tetrazolyl, triazolyl, oxadiazolyl, benzimidazolyl, purinyl, pyrazolyl, pyrazinyl, pteridinyl, quinoxalinyl, phthalazinyl, quinazolinyl, triazinyl, phenazinyl, cinnolinyl, pyrimidinyl, pyridazinyl, or a combination thereof.

As used herein in the context of any moiety, the term "substituted" can mean that one or more hydrogens on the designated atom or group are replaced with another group provided that the designated atom's normal valence is not exceeded. For example, when the substituent is oxo (i.e., =O), then two hydrogens on the atom are replaced. In certain embodiments, the substituent is halo (e.g., fluoro, chloro, bromo, iodo), hydroxyl, cyano, nitro, alkoxy, amino, aryl, heteroaryl, alkyl, heteroalkyl, oxo, or combinations thereof. Combinations of substituents and/or variables are permissible provided that the substitutions do not significantly adversely affect synthesis or use of the compound. The substituted moiety typically comprises at least one substituent (e.g., 1, 2, 3, 4, 5, 6, etc.) in any suitable position (e.g., 1-, 2-, 3-, 4-, 5-, or 6-position, etc.).

The oxidized intermediate produced in step (a) can be any suitable oxidized intermediate. Generally, the oxidized intermediate is any compound formed through the process of an oxidation step, an oxygenation step, or a combination thereof. In some embodiments, the oxidized intermediate is an alcohol, carboxylic acid, ester, or a combination thereof. In certain embodiments, the oxidized intermediate has undergone a displacement and/or dehydration with an oxygen acid to produce a modified product, such as an ester. In certain embodiments, the oxidized intermediate has undergone a hydration reaction to produce a modified product, such as an alcohol. In certain instances, the oxidized intermediate is oxidized in at least one position, for example, the oxidized intermediate can be oxidized in two different positions or more, three different positions or more, four different positions or more, or five different positions or more. In some embodiments, the oxidized intermediate has been oxidized in two or more (e.g., 3 or more, 4 or more, or 5 or more) different positions with the same functional group. In other embodiments, the oxidized intermediate has been oxidized in two or more (e.g., 3 or more, 4 or more, or 5 or more) different positions with at least two different functional groups.

In some embodiments, the oxidized intermediate is an alkyl electrophile intermediate. As used herein, the term "alkyl electrophile intermediate" refers to an intermediate where the oxidizing electrophile has undergone an electrophilic C—H activation ("CHA") reaction to produce a metal-carbon bond. Without wishing to be bound by any particular theory, it is believed that the alkyl electrophile intermediate can proceed to form an oxidized intermediate, or can undergo an elimination reaction to produce the alkene according to aspects of the invention described here.

As used herein, the term "alkene" refers to any organic molecule comprising at least two adjacent $sp^2$ hybridized carbon atoms with a carbon-carbon double bond between them (i.e., an alkenyl-containing compound). The adjacent $sp^2$ hybridized carbon atoms can be derived from two adjacent $sp^3$ hybridized carbon atoms that have been oxidized. For example, the alkene can be substituted, unsubstituted, branched, straight-chained, cyclic, or a combination thereof, and can be fully unsaturated or includes portions that are saturated or aromatic, provided that the alkene has at least one $sp^2$ hybridized carbon atom adjacent to a second $sp^2$ hybridized carbon atom. Accordingly, the alkene can be a $C_2$-$C_{20}$ alkene, a $C_2$-$C_{20}$ heteroalkene, $C_3$-$C_{20}$ cycloalkene, $C_3$-$C_{20}$ heterocycloalkene, arylalkene, heteroarylalkene, or a combination thereof In further embodiments, the alkene is ethylene, propene, butene, or a mixture thereof. Thus, the definitions of $C_2$-$C_{20}$ alkane, $C_2$-$C_{20}$ heteroalkane, $C_3$-$C_{20}$ cycloalkane, $C_3$-$C_{20}$ heterocycloalkane, arylalkane, heteroarylalkane, as described herein, apply to $C_2$-$C_{20}$ heteroalkene, $C_3$-$C_{20}$ cycloalkene, $C_3$-$C_{20}$ heterocycloalkene, arylalkene, heteroarylalkene as long as the $C_2$-$C_{20}$ alkane, $C_2$-$C_{20}$ heteroalkane, $C_3$-$C_{20}$ cycloalkane, $C_3$-$C_{20}$ heterocycloalkane, arylalkane, or heteroarylalkane comprises at least one olefin moiety.

The oxidizing electrophile comprises a main group element. The main group element (M) typically includes elements in the post-transition metal and non-metal groups of the periodic table and include, for example, elements with atomic numbers 31, 32, 33, 34, 35, 49, 50, 51, 52, 53, 81, 82, and 83. In an embodiment, the term "main group element" typically refers to any element having filled 4d or 5d orbitals, which undergoes a net one- or two-electron change in oxidation state. Suitable main group elements include thallium, indium, lead, antimony, mercury, tin, selenium, tellurium, arsenic, cadmium, iodine, and bismuth. In some embodiments, the main group element is antimony, tellurium, bismuth, or arsenic. In some embodiments, the oxidizing electrophile comprises iodine. In further embodiments, the oxidizing electrophile comprises Sb(V), Te(VI), Te(IV), Bi(V), Se(VI), Se(IV), As(V), I(V), I(III), or Sn(IV).

The process comprises contacting the alkane with an oxidizing electrophile comprising a main group element in oxidized form. The main group element in oxidized form can be any suitable main group element in any suitable oxidation state, as described herein. For example, the main group element can have an oxidation state of +7, +6, +5, +4, +3, +2, or +1, particularly an oxidation state of +6, +5, +4, +3, or +2. In preferred embodiments, the main group element in oxidized form has any oxidation state suitable for a one- or two-electron reduction/oxidation process.

In some embodiments, the process comprises contacting the alkane with an oxidant and a reduced form of an oxidizing electrophile. As used herein, "a reduced form of the oxidizing electrophile" refers to any reduced form of an oxidizing electrophile comprising a main group element. Generally, the reduced form of the oxidizing electrophile comprises a main group element with a one- or two-electron difference in oxidation state, relative to the oxidizing electrophile comprising a main group element in oxidized form. For example, the reduced form of the oxidizing electrophile will have a main group element in an oxidation state of +6, +5, +4, +3, +2, or +1, or a neutral oxidation state. In certain embodiments, the reduced form of the oxidizing electrophile comprises the main group element in an oxidation state of +4, +3, +2, or +1, or a neutral oxidation state. In some embodiments, the reduced form of the oxidizing electrophile can be any suitable chemical variant of the oxidizing electrophile, such that the main group element has been reduced by one or two electrons, preferably two electrons.

In embodiments where the process comprises contacting the alkane with an oxidant and a reduced form of an oxidizing electrophile, the oxidant can be any suitable oxidant capable of generating the main group element in oxidized form. For example, the oxidant (e.g., the oxidizing regeneration reagent) can be molecular oxygen, air, a peroxide, nitric oxide, nitrous oxide, nitric acid, sulfur trioxide, ozone, or a combination thereof. The oxidant can be used under an inert atmosphere or in combination with air. The peroxide can be, e.g., an organic peroxide, inorganic peroxide, hydrogen peroxide, or a combination thereof. In some embodiments, the oxidant can be an organic oxidant. For example, the oxidant can be a quinone or a nitroxide. In certain embodiments, the oxidant is molecular oxygen, air, ozone, hydrogen peroxide, organoperoxide, nitric acid, or a combination thereof.

In certain embodiments, the oxidizing electrophile comprises at least one conjugate anion of an oxygen acid. For example, the oxidizing electrophile can comprise 1, 2, 3, 4, 5, or 6 conjugate anions of an oxygen acid. As used herein, "oxygen acid" refers to any organic acid or inorganic acid which contains hydrogen, oxygen, and at least one other element, in which the protic hydrogen is attached to oxygen. Generally, the conjugate anion of an oxygen acid is selected from sulfite, sulfate, hydrogen sulfate, thiosulfate, nitrite, nitrate, phosphate, phosphite, hydrogen phosphate, dihydrogen phosphate, carbonate, hydrogen carbonate, oxalate, cyanate, isocyanate, chromate, dichromate, permanganate, carboxylate, sulfonate, borate, and any combination thereof.

In some embodiments, the conjugate anion of an oxygen acid is an electron-deficient alkoxide, aryloxide, or a combination thereof. As used herein, the term "electron-deficient alkoxide" refers to any alkoxide with at least one electron withdrawing substituent as described here. For example, the electron-deficient alkoxide can be trifluoroethoxide. As used herein, the term "aryloxide" refers to any oxide with an optionally substituted aryl group as described herein. For example, the electron-deficient aryloxide can be phenoxide with electron-withdrawing groups on the ring.

In some embodiments, the conjugate anion of an oxygen acid is a carboxylate, a sulfate, a sulfonate, a phosphate, a borate, or a combination thereof, each of which is optionally substituted. Typically, the carboxylate can be an aliphatic carboxylate (e.g., acetate), an aromatic carboxylate or a fluorinated carboxylate (e.g., trifluoroacetate (TFA)). Similarly, the sulfonate can be an aliphatic sulfonate (e.g., methanesulfonate), an aromatic sulfonate, or a fluorinated sulfonate (e.g., trifluoromethanesulfonate). The conjugate anion of the oxygen acid can be an aliphatic carboxylate, heteroaliphatic carboxylate, aromatic carboxylate, heteroaromatic carboxylate, aliphatic sulfonate, heteroaliphatic sulfonate, aromatic sulfonate, heteroaromatic sulfonate, aliphatic phosphate, heteroaliphatic phosphate, aromatic phosphate, heteroaromatic phosphate, aliphatic borate, heteroaliphatic borate, aromatic borate, heteroaromatic borate, or a mixture thereof. In some embodiments, the conjugate anion of the oxygen acid is trifluoroacetate, acetate, alkylsulfonate, phosphate, nitrate, sulfate, trifluoromethanesulfate, or fluorosulfate.

As used herein, "aliphatic" refers to a substituted or unsubstituted $C_1$-$C_9$ alkyl substituent, in which, "$C_1$-$C_9$ alkyl" refers to an alkyl carbon chain from 1 to 9 (i.e., 1, 2, 3, 4, 5, 6, 7, 8, or 9) carbons in length. In some embodiments, $C_1$-$C_9$ alkyl can be saturated, unsaturated, branched, straight-chained, cyclic, or a combination thereof. An exemplary, but non-limiting list of $C_1$-$C_9$ alkyl aliphatics includes methyl, ethyl, n-propyl, iso-propyl, n-butyl, sec-butyl, tent-butyl, n-pentyl, sec-pentyl, neo-pentyl, hexyl, heptyl, octyl, nonyl, cyclopentyl, cyclohexyl, propenyl, 2-butenyl, 3-butenyl, 2-pentenyl, 3-pentenyl, 4-pentenyl, or a combination thereof In certain embodiments, the aliphatic group is perfluorinated.

As used herein, "heteroaliphatic" refers to a substituted or unsubstituted $C_1$-$C_9$ alkyl substituent which contains at least 1 heteroatom (e.g., O, S, N, and/or P) in the core of the molecule (i.e., the carbon backbone). The $C_1$-$C_9$ alkyl substituent can be saturated, unsaturated, branched, straight-chained, cyclic, or a combination thereof In certain instances, the heteroaliphatic substituent has at least 2 heteroatoms in the core of the molecule (e.g., at least 3, 4, 5, or 6 heteroatoms in the core of the molecule). In some embodiments, the heteroaliphatic compound is an ether, an ester, a carbonate, an amide, an amine, a carbamate, a thioether, a thioester, a phosphate, a heterocycloalkane, or a combination thereof In certain embodiments, the heteroaliphatic group is perfluorinated.

As used herein, "aromatic" refers to a substituted or unsubstituted, monocyclic or polycyclic aromatic substituent. An exemplary, but non-limiting list of aromatic substituents includes phenyl, xylenyl, naphthyl, biphenyl, anthracyl, or a combination thereof In certain embodiments, the aromatic group is perfluorinated.

As used herein, "heteroaromatic" refers to a substituted or unsubstituted, monocyclic or polycylic aromatic compound, which has at least one heteroatom (e.g., O, S, or N) in at least one of the rings. In certain embodiments, the heteroaromatic substituent is polycyclic and has 2, 3, or 4 aromatic rings. Each ring of the heteroaromatic substituent containing a heteroatom can contain one or two oxygen and/or sulfur atoms and/or from one to four nitrogen atoms, provided that the total number of heteroatoms in each ring is 4 or less and each ring has at least one carbon atom. The fused rings completing the polycyclic groups can contain only carbon atoms and can be saturated, partially saturated, or unsaturated. The nitrogen and sulfur atoms can optionally be oxidized, and the nitrogen atoms can optionally be quaternized. Heteroaromatic substituents that are polycyclic must include at least one fully aromatic ring but the other fused ring(s) can be aromatic or non-aromatic. In some embodiments, the heteroaromatic substituent is pyrrolyl, isoindolyl, indolizinyl, indolyl, furanyl, benzofuranyl, benzothiophenyl, thiophenyl, pyridyl, acridinyl, naphthyridinyl, quinolinyl, isoquinolinyl, isoxazolyl, oxazolyl, benzoxazolyl, isothiazolyl, thiazolyl, benzthiazolyl, imidazolyl, thiadiazolyl, tetrazolyl, triazolyl, oxadiazolyl, benzimidazolyl, purinyl, pyrazolyl, pyrazinyl, pteridinyl, quinoxalinyl, phthalazinyl, quinazolinyl, triazinyl, phenazinyl, cinnolinyl, pyrimidinyl, pyridazinyl, or a combination thereof In certain embodiments, the heteroaromatic group is perfluorinated.

In some embodiments, the oxidizing electrophile is of the formula $M^{+n}X_pL_q$, wherein M is a main group element cation cation in an oxidation state of n, X is the conjugate anion of the oxygen acid, L is a ligand, n is an integer from 2 to 6 (i.e., 2, 3, 4, 5, or 6), p is an integer from 1 to 6 (i.e., 1, 2, 3, 4, 5, or 6), and q is an integer from 0 to 5 (i.e., 0, 1, 2, 3, 4, or 5). The oxidizing electrophile of the formula $M^{+n}X_pL_q$ can have any suitable net charge. For example, the oxidizing electrophile of the $M^{+n}X_pL_q$ can have a net charge of +5, +4, +3, +2, or +1, or a neutral net charge. In certain embodiments, the oxidizing electrophile of the formula $M^{+n}X_pL_q$ is a neutral species. Without wishing to be bound to any particular theory, the reactive species $[M^{+n}X_p]$ can have up to q number of ligands (L) to either balance the net charge of $[M^{+n}X_p]$ and/or solvate the remaining charge of $[M^{+n}X_p]$. In some embodiments, $M^{+n}X_pL_q$ undergoes reaction with the alkane in the liquid medium to yield a reduced form of the oxidizing electrophile of formula $M^{+(n-2)}X_{p-2}L_q$ or $M^{+(n-1)}X_{p-1}L_q$. In certain embodiments, n and p are the same or different and each is an integer from 2 to 6 (i.e., 2, 3, 4, 5, 6), and q is an integer from 0 to 4 (i.e., 0, 1, 2, 3, or 4).

X of any of the foregoing formulas can be any suitable conjugate anion of an oxygen acid, as described herein, in any suitable oxidation state. Generally, X is one or more selected from an aliphatic carboxylate, heteroaliphatic carboxylate, aromatic carboxylate, heteroaromatic carboxylate, aliphatic sulfonate, heteroaliphatic sulfonate, aromatic sulfonate, heteroaromatic sulfonate, aliphatic phosphate, heteroaliphatic phosphate, aromatic phosphate, heteroaromatic phosphate, aliphatic borate, heteroaliphatic borate, aromatic borate, and heteroaromatic borate. As used herein, carboxylates can be alkylated variants (e.g., acetate), fluorinated variants (e.g., trifluoroacetate (TFA)), or arylated variants (e.g., benzoates or benzoic acids). As used herein, "alkylated variants" and "arylated variants" refer to a carboxylic acid containing an alkyl group or an aryl group, respectively, as defined herein. Similarly, sulfonates can be alkylated variants (e.g., methanesulfonate) or fluorinated variants (e.g., trifluoromethanesulfonate). In certain embodiments, X is one or more selected from trifluoroacetate, acetate, benzoate, sulfate, methanesulfonate, and trifluoromethanesulfonate. Typically, X has an oxidation state of −4, −3, −2, or −1.

The ligand (L) can be any ligand that suitably coordinates to the main group element (M). Generally, each ligand is the same or different and each can be anionic or neutral. In some embodiments, each ligand (L) is independently an oxide (e.g., a bridging oxide (bridging oxo) or a terminal oxide (terminal oxo)), hydroxide, or combination thereof. In certain embodiments, the ligand is anionic and helps balance the charge of the oxidizing electrophile. In certain embodiments, the ligand is neutral and helps solvate the charge of the oxidizing electrophile. In some embodiments, the ligand is the non-oxidizable liquid (e.g., solvent), an alkene molecule, a product of the alkene oxidation, or a combination thereof.

In some embodiments, the ligand is at least one monodentate or bidentate ligand that is aliphatic-based or aromatic-based and comprises at least one oxo, amino, thiol, sulfonyl, or carboxyl group, and optionally comprises one or more electron withdrawing groups, as described herein. In certain embodiments, the ligand comprises at least one carboxyl group. As used herein, "aliphatic-based" or "aromatic-based" refer to the ligand as a whole, and the ligand can be bound directly to the aliphatic or aromatic portion, or indirectly via at least one oxo, amino, thiol, sulfonyl, or carboxyl group. The terms "aliphatic" and "aromatic" are as described herein.

In certain embodiments, the ligand is aromatic-based. In embodiments where the ligand is aromatic-based, the ligand can comprise at least one carboxyl group and/or at least one nitro group.

In certain embodiments, the ligand is selected from the group consisting of:

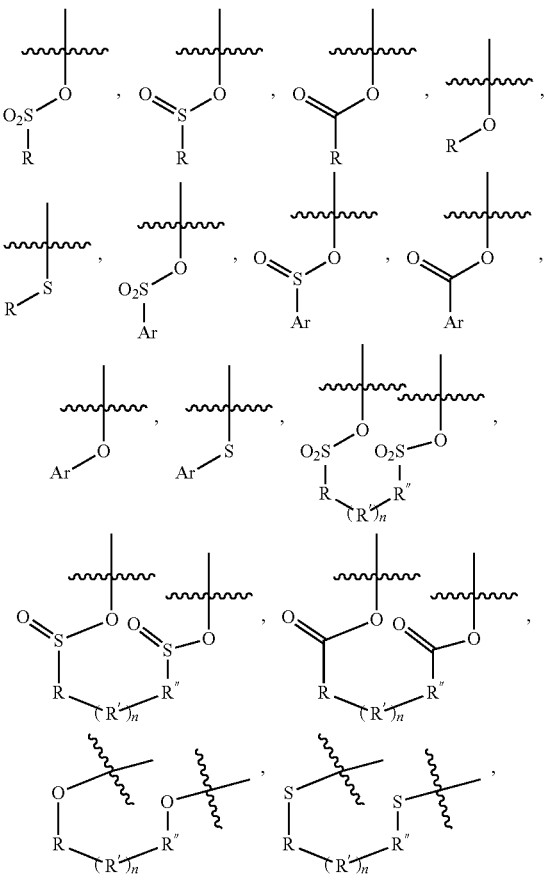

-continued

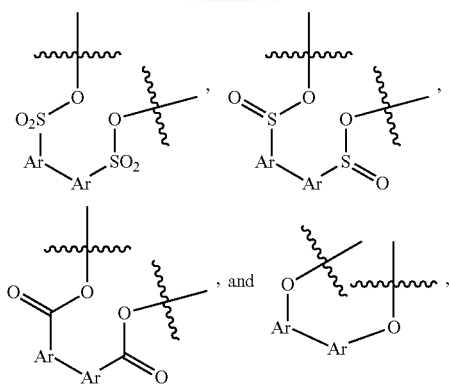

wherein R, R', and R" are the same or different and each is an optionally substituted alkyl, Ar is an optionally substituted aryl, and n is 0 or an integer of 1 to 6.

The ligand also can be of the formula —Ar—EWG, wherein Ar is an optionally substituted aryl and EWG is at least one electron withdrawing group, as described herein. For example, the electron withdrawing group can be at least one moiety selected from —$NO_2$, fluoro-$C_{1-8}$ alkyl, —F, —OOCR, —COOH, —$OH_2^+$, —$CONH_2$, —COOR, —$NR_3^+$, —CN, —$SO_3H$, —$SO_3R$, —$SO_3W$, and a combination thereof. In the context of the electron withdrawing group, R is hydrogen or any aliphatic (e.g., $C_{-8}$ alkyl, fluoro-$C_{1-8}$ alkyl), heteroaliphatic, aromatic, or heteroaromatic moiety, each of which is optionally substituted, and W is a cation comprising a metal selected from boron, bismuth, antimony, arsenic, lanthanum, cerium, scandium, yttrium, titanium, zirconium, hafnium, silver, zinc, cadmium, aluminum, gallium, indium, germanium, tin, phosphorus, an alkali metal, or an alkaline earth metal.

For example, the ligand can be:

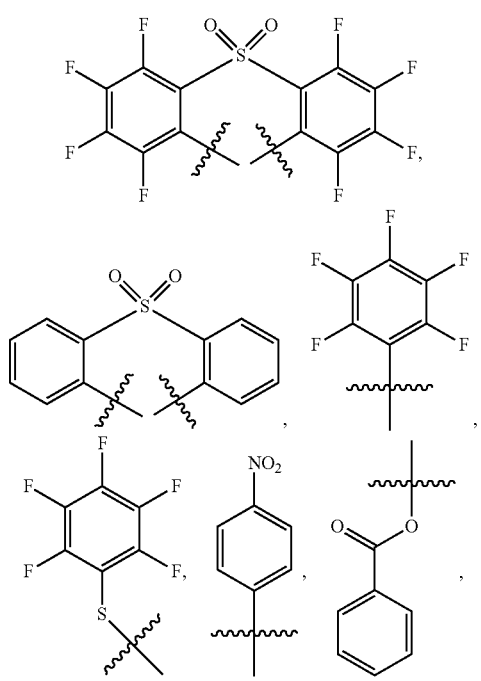

-continued

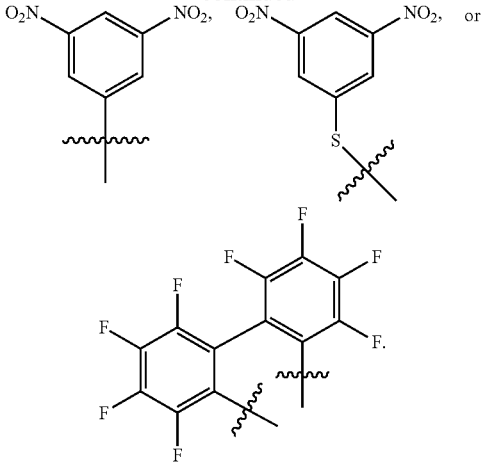

Figure 2:
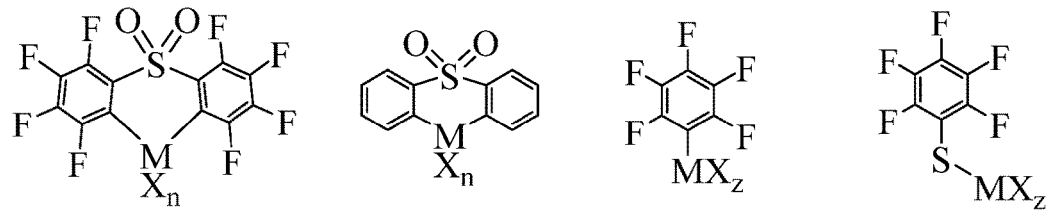
FIG. 2 is a list of exemplary oxidizing electrophiles.
Figure 2:
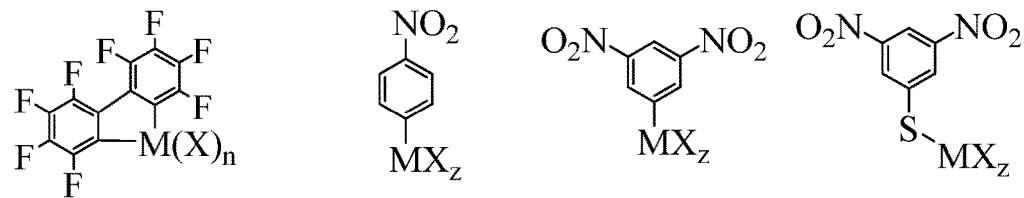

In some embodiments, the oxidizing electrophile has a formula according to any one of the structures in FIG. 2.

The oxidizing electrophile can be prepared using any suitable method. For example, the oxidizing electrophile can be prepared separately as a stable and isolable compound or the oxidizing electrophile can be generated in situ from a reduced form of the oxidizing electrophile, generated in situ through a substitution reaction, or generated in situ through a dehydration reaction. A combination of any of these methods can also be used.

The ligand can be present in the mixture in less than stoichiometric quantities relative to the main group element, stoichiometric quantities relative to the main group element, or at least stoichiometric quantities relative to the main group element.

In some embodiments, the oxidizing electrophile, in either oxidized or reduced form, is present in at least stoichiometric quantities relative to the amount of alkene produced (e.g., relative to the amount of alkane that reacts). Typically, when the oxidizing electrophile is present in at least a stoichiometric quantity relative to the alkene, an oxidizing regeneration reagent is not present in the reaction. In other embodiments, the oxidizing electrophile, in either oxidized or reduced form, is present in a sub-stoichiometric quantity relative to the alkane. Typically, when the oxidizing electrophile is present in a sub-stoichiometric quantity, an oxidizing regeneration reagent and optionally an oxidative regeneration catalyst are present to regenerate the oxidizing electrophile from the reduced form of the oxidizing electrophile. In some preferred embodiments, the oxidizing electrophile, in either oxidized or reduced form, is present in at least a stoichiometric quantity relative to the alkene produced and an oxidizing regeneration reagent and optionally an oxidative regeneration catalyst are not required, but can be present in the liquid medium. In other preferred embodiments, the oxidizing electrophile is present in a sub-stoichiometric quantity relative to the alkene produced and an oxidizing regeneration reagent or an oxidative regeneration catalyst are present. In some embodiments, the oxidizing electrophile is present in sub-stoichiometric quantities relative to the alkene produced and acts as a catalyst.

In the process, the reduced form of the oxidizing electrophile is generated in situ from the reduction of the oxidizing electrophile upon formation of alkene. The reduced form of the oxidizing electrophile can, if desired, be used to regenerate the oxidizing electrophile. In some embodiments, the reduced form of the oxidizing electrophile is provided directly to the process for converting an alkane to an alkene. In these instances, the reduced form of the oxidizing electrophile is used to generate the oxidizing electrophile. Accordingly, when the reduced form of the oxidizing electrophile is provided directly to the process in at least stoichiometric quantities or sub-stoichiometric quantities, the oxidant is present in the reaction mixture to generate the oxidizing electrophile.

Thus, the process for converting an alkane to an alkene can comprise the oxidizing electrophile, the reduced form of the oxidizing electrophile, or both the oxidizing electrophile and the reduced form of the oxidizing electrophile. The amount of the oxidizing electrophile and/or the reduced form of the oxidizing electrophile is not particularly limited such that a sufficient amount of the oxidizing electrophile exists to convert alkane to alkene. Accordingly, the oxidizing electrophile and/or the reduced form of the oxidizing electrophile can be present in an amount of about 0.1 mol % of the alkane or more (e.g., about 0.2 mol % or more, about 0.3 mol % or more, about 0.4 mol % or more, about 0.5 mol % or more, about 1 mol % or more, about 2 mol % or more, about 3 mol % or more, about 5 mol % or more, about 10 mol % or more, about 20 mol % or more, about 50 mol % or more, or about 100 mol % or more). Alternatively, or in addition, the oxidizing electrophile and/or the reduced form of the oxidizing electrophile can be present in an amount of about 2000 mol % of the alkane or less (e.g., about 1500 mol % or less, about 1000 mol % or less, about 900 mol % or less, about 800 mol % or less, about 700 mol % or less, about 600 mol % or less, about 500 mol % or less, about 400 mol % or less, about 300 mol % or less, about 200 mol % or less, or about 100 mol % or less). Any two of the foregoing endpoints can be used to define a close-ended range, or any single endpoint can be used alone to define an open-ended range. For example, the oxidizing electrophile and/or the reduced form of the oxidizing electrophile can be present in an amount between about 0.1 mol % to about 2000 mol % of the alkane, for example, about 0.1 mol % to about 1500 mol %, about 0.1 mol % to about 1000 mol %, about 0.1 mol % to about 900 mol %, about 0.1 mol % to about 800 mol %, about 0.1 mol % to about 700 mol %, about 0.1 mol % to about 600 mol %, about 0.1 mol % to about 500 mol %, about 0.1 mol % to about 400 mol %, about 0.1 mol % to about 300 mol %, about 0.1 mol % to about 200 mol %, about 0.1 mol % to about 100 mol %, about 0.2 mol % to about 100 mol %, about 0.3 mol % to about 100 mol %, about 0.4 mol % to about 100 mol %, about 0.5 mol % to about 100 mol %, about 1 mol % to about 100 mol %, about 2 mol % to about 100 mol %, about 3 mol % to about 100 mol %, about 5 mol % to about 100 mol %, about 10 mol % to about 100 mol %, about 20 mol % to about 100 mol %, about 50 mol % to about 100 mol %, about 100 mol % to about 1000 mol %, or about 100 mol % to about 600 mol %.

In some embodiments of the process, the liquid medium comprises an oxygen acid, such as aliphatic carboxylic acid, heteroaliphatic carboxylic acid, aromatic carboxylic acid, heteroaromatic carboxylic acid, aliphatic sulfonic acid, heteroaliphatic sulfonic acid, aromatic sulfonic acid, heteroaromatic sulfonic acid, aliphatic phosphonic acid, heteroaliphatic phosphonic acid, aromatic phosphonic acid, heteroaromatic phosphonic acid, boric acid, aliphatic boronic acid, heteroaliphatic boronic acid, aromatic boronic acid, heteroaromatic boronic acid, or a mixture thereof In certain embodiments, the oxygen acid is trifluoroacetic acid, acetic acid, methanesulfonic acid, phosphoric acid, nitric acid, sulfuric acid, trifluoromethanesulfonic acid, fluorosulfuric acid, or a mixture thereof In some embodiments, the oxygen acid is an electron-deficient alcohol, an aryl alcohol, or a combination thereof As used herein, the term "electron-deficient alcohol" refers to any alcohol with at least one electron withdrawing substituent, as described herein. For example, the electron-deficient alcohol can be trifluoroethanol. As used herein, the term "aryl alcohol" refers to any alcohol with an aryl group, as described herein. For example, the aryl alcohol can be phenol.

In further embodiments, all or a portion of the oxygen acid is added as an anhydride of the oxygen acid. In preferred embodiments, a portion of the oxygen acid is added as an anhydride. Without wishing to be bound by any particular theory, it is believed that the anhydride can act as a water scavenger, resulting in a reduced amount of water in the liquid medium and in turn generating two molecules of the oxygen acid for every one molecule of water and anhydride.

The oxygen acid can be present in an amount of about 0.1 mol % of the oxidizing electrophile or more (e.g., about 0.2 mol % or more, about 0.3 mol % or more, about 0.4 mol % or more, about 0.5 mol % or more, about 1 mol % or more, about 2 mol % or more, about 3 mol % or more, about 5 mol % or more, about 10 mol % or more, about 20 mol % or more, about 50 mol % or more, or about 100 mol % or more). Alternatively, or in addition, the oxygen acid can be present in an amount of about 2000 mol % of the oxidizing electrophile or less (e.g., about 1500 mol % or less, about 1000 mol % or less, about 900 mol % or less, about 800 mol % or less, about 700 mol % or less, about 600 mol % or less, about 500 mol % or less, about 400 mol % or less, about 300 mol % or less, about 200 mol % or less, or about 100 mol % or less). Any two of the foregoing endpoints can be used to define a close-ended range, or can be used alone to define an open-ended range. Thus, the oxygen acid can be present in an amount between about 0.1 mol % to about 2000 mol % of the oxidizing electrophile, for example, about 0.1 mol % to about 1500 mol %, about 0.1 mol % to about 1000 mol %, about 0.1 mol % to about 900 mol %, about 0.1 mol % to about 800 mol %, about 0.1 mol % to about 700 mol %, about 0.1 mol % to about 600 mol %, about 0.1 mol % to about 500 mol %, about 0.1 mol % to about 400 mol %, about 0.1 mol % to about 300 mol %, about 0.1 mol % to about 200 mol %, about 0.1 mol % to about 100 mol %, about 0.2 mol % to about 100 mol %, about 0.3 mol % to about 100 mol %, about 0.4 mol % to about 100 mol %, about 0.5 mol % to about 100 mol %, about 1 mol % to about 100 mol %, about 2 mol % to about 100 mol %, about 3 mol % to about 100 mol %, about 5 mol % to about 100 mol %, about 10 mol % to about 100 mol %, about 20 mol % to about 100 mol %, about 50 mol % to about 100 mol %, about 100 mol % to about 1000 mol %, or about 100 mol % to about 600 mol %.

Depending on the embodiment, the liquid medium can comprise one or more additives, such as a non-oxidizable liquid, a salt additive, a Lewis acid, and water. Desirably, the additives can be used to provide a functional benefit to the reaction mixture (e.g., liquid medium), such as solvation, solubilization, viscosity modification, and/or charge transfer.

The amount of additive is not particularly limited such that the additive can be used in amounts that are a fraction of the amount of oxidizing electrophile or in amounts that are in a large excess of the amount of oxidizing electrophile. The one or more additives can be present in an amount of about 0.1 mol % of the oxidizing electrophile or more (e.g., about 0.2 mol % or more, about 0.3 mol % or more, about 0.4 mol % or more, about 0.5 mol % or more, about 1 mol % or more, about 2 mol % or more, about 3 mol % or more, about 5 mol % or more, about 10 mol % or more, about 20 mol % or more, about 50 mol % or more, or about 100 mol % or more). Alternatively, or in addition, the one or more additives can be present in an amount of about 2000 mol % of the oxidizing electrophile or less (e.g., about 1500 mol % or less, about 1000 mol % or less, about 900 mol % or less, about 800 mol % or less, about 700 mol % or less, about 600 mol % or less, about 500 mol % or less, about 400 mol % or less, about 300 mol % or less, about 200 mol % or less, or about 100 mol % or less). Any two of the foregoing endpoints can be used to define a close-ended range, or a single point can be used alone to define an open-ended range. Thus, the one or more additives can be present in an amount between about 0 mol % to about 2000 mol % of the oxidizing electrophile, for example, about 0 mol % to about 1500 mol %, about 0 mol % to about 1000 mol %, about 0 mol % to about 900 mol %, about 0 mol % to about 800 mol %, about 0 mol % to about 700 mol %, about 0 mol % to about 600 mol %, about 0 mol % to about 500 mol %, about 0 mol % to about 400 mol %, about 0 mol % to about 300 mol %, about 0 mol % to about 200 mol %, about 0 mol % to about 100 mol %, about 0.1 mol % to about 100 mol %, about 0.2 mol % to about 100 mol %, about 0.3 mol % to about 100 mol %, about 0.4 mol % to about 100 mol %, about 0.5 mol % to about 100 mol %, about 1 mol % to about 100 mol %, about 2 mol % to about 100 mol %, about 3 mol % to about 100 mol %, about 5 mol % to about 100 mol %, about 10 mol % to about 100 mol %, about 20 mol % to about 100 mol %, about 50 mol % to about 100 mol %, about 100 mol % to about 1000 mol %, or about 100 mol % to about 600 mol %. In some embodiments, the additive is not present (i.e., about 0 mol % or below the level of detection) in the liquid medium.

In some embodiments, the liquid medium comprises at least one non-oxidizable liquid. The non-oxidizable liquid can be any suitable liquid (e.g., fluid or solvent) such that the liquid does not interfere with the process for converting an alkane to an alkene. In some embodiments, the oxidized intermediate is the non-oxidizable liquid (e.g., fluid or solvent).

In certain embodiments, the liquid can be considered substantially inert under the reaction conditions. In some embodiments, the liquid is substantially inert in the presence of the oxidizing electrophile.

As used herein, "substantially inert" refers to a liquid (e.g., fluid or solvent) that maintains greater than about 80% stability in the presence of the oxidizing electrophile, such as measured by the retention of the non-oxidizable liquid peaks in a $^1$H Nuclear Magnetic Resonance (NMR) spectrum, relative to a standard. In certain embodiments, the liquid can maintain greater than about 85% stability in the presence of the oxidizing electrophile, for example, greater than about 90% stability in the presence of the oxidizing electrophile, greater than about 92% stability in the presence of the oxidizing electrophile, greater than about 94% stability in the presence of the oxidizing electrophile, greater than about 95% stability in the presence of the oxidizing electrophile, greater than about 98% stability in the presence of the oxidizing electrophile, or greater than about 99% stability in the presence of the oxidizing electrophile. Ideally, the liquid is totally inert to the oxidizing conditions but with strong oxidants, it can be expected that a small amount of liquid may be consumed or lost in subsequent recycle steps.

As used herein, the terms "liquid" or "liquid medium" refer to any medium that comprises a liquid. For example, the liquid or liquid medium can exist as a liquid-solid medium, a liquid-gas medium, a liquid-liquid medium, a liquid-gas-solid medium, etc. Accordingly, the liquid or liquid medium can be, for example, a solution, a gas-sparged liquid, a gel, a colloid, a slurry, a dispersion, an emulsion, or a combination thereof In some embodiments, the non-oxidizable liquid is selected from a fluorinated hydrocarbon, a sulfone, a deactivated arene, a deactivated aliphatic, a deactivated heteroarene, a deactivated heteroaliphatic, a carbonate, or a combination thereof In some embodiments, the non-oxidizable liquid is one or more suitable fluorinated hydrocarbon(s). The fluorinated hydrocarbon can be at least one fluorinated or perfluorinated straight chain aliphatic comprising at least 2 carbons, for example, at least 3, 4, 5, 6, 7, 8, 9, 10, 11, 12, 13, 14, 15, or 16 carbons. Preferably, the fluorinated hydrocarbon is at least one fluorinated or perfluorinated cyclic aliphatic comprising at least 3 carbons, for example, at least 4, 5, 6, 7, 8, 9, or 10 carbons. In some embodiments, the fluorinated or perfluorinated cyclic aliphatic can be monocyclic, bicyclic, or tricyclic. The fluorinated hydrocarbon can be perfluorinated and is branched or straight, and either substituted or unsubstituted. Preferably, the fluorinated or perfluorinated straight chain aliphatic and/or the fluorinated or perfluorinated cyclic aliphatic is substituted with one or more aliphatic substituents. More preferably, the fluorinated hydrocarbon is perfluorinated.

Specific examples include perfluropentane, perfluorohexane, perfluoroheptane, perfluorooctane, perfluorononane, perfluorodecane, perfluorocyclohexane, perfluorocycloheptane, perfluorocyclooctane, perfluorodecalin, perfluoromethylcyclohexane, perfluorodimethylcyclohexane, perfluorotrimethylcyclohexane, perfluoroethylcyclohexane, perfluorodiethylcyclohexane, perfluorotriethylcyclohexane, perfluoroethylmethylcyclohexane, and perfluoro-2,2,3,3-tetramethylbutane.

In some embodiments, the non-oxidizable liquid is one or more sulfone(s) of the formula:

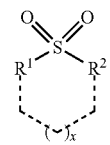

in which $R^1$ and $R^2$ are independently chosen from an aryl group and alkyl group, each of which is optionally substituted, the dashed lines represent optional bonds and atoms (e.g., C, N, O, S, or P), and x is an integer from 0 to 3 (i.e., 0, 1, 2, or 3). In certain embodiments, $R^1$ and $R^2$ are connected by a chain to produce a cyclic sulfone.

In some embodiments, the sulfone is at least one alkyl sulfone, in which both $R^1$ and $R^2$ are independently chosen as alkyl groups. The alkyl group can be any suitable straight chain, branched, or cyclic alkyl group (e.g., $C_{1-9}$ alkyl). In certain embodiments, the alkyl group is substituted with at least 1 electron withdrawing substituent (e.g., at least 2, 3, or 4 electron withdrawing substituents), such as those described herein. In certain embodiments, the alkyl groups are connected by an alkylene chain to produce a cyclic alkyl sulfone, such as sulfolane.

As used herein, "alkyl" refers to an aliphatic substituent that can be substituted, unsubstituted, branched, straight-chained, cyclic, or a combination thereof, and can be fully saturated or include portions that are unsaturated or aromatic. In some embodiments, the alkyl is $C_1$-$C_9$ alkyl, such as methyl, ethyl, n-propyl, iso-propyl, n-butyl, sec-butyl, tert-butyl, n-pentyl, sec-pentyl, neo-pentyl, hexyl, heptyl, octyl, nonyl, cyclopentyl, cyclohexyl, propenyl, 2-butenyl, 3-butenyl, 2-pentenyl, 3-pentenyl, 4-pentenyl, or a combination thereof In some embodiments, the alkyl is a heteroalkyl group, a cycloalkyl group, or a heterocycloalkyl group.

As used herein, "heteroalkyl" refers to a substituted or unsubstituted alkyl which contains at least 1 heteroatom (e.g., O, S, N, and/or P) in the core of the molecule (i.e., any part of the molecule except for the alkane-containing portion). Accordingly, at least 1 heteroatom can be a pendant substituent or part of a carbon chain. In certain instances, the heteroalkyl group has at least 2 heteroatoms in the core of the molecule (e.g., at least 3, 4, 5, or 6 heteroatoms in the core of the molecule). In some embodiments, the heteroalkyl group comprises a moiety selected from an ether, an ester, a carbonate, an amide, an amine, a carbamate, a thioether, a thioester, a phosphate, a heterocycloalkane, a haloalkane, an acetyl, an alcohol, a ketone, an aldehyde, a carboxylate, a carboxylic acid, a hemiacetal, an acetal, a ketal, an imine, and imide, a thiol, a disulfide, a sulfoxide, a thioketone, or a combination thereof.

The term "cycloalkyl," as used herein, refers to a substituted or unsubstituted alkyl group comprising a cyclic alkane moiety containing from, for example, 3 to 6 carbon atoms or from 5 to 6 carbon atoms. In some embodiments, the cycloalkyl group is cyclopropyl, cyclobutyl, cyclopentyl, or cyclohexyl. In some embodiments, the cycloalkyl can be a cycloalkenyl, as long as the cycloalkenyl comprises an alkane-containing portion. The term "cycloalkenyl" refers to a cycloalkane, as described herein, with at least one C-C double bond in the ring. For example, the cycloalkenyl can be cyclopentenyl or cyclohexenyl.

The term "heterocycloalkyl," as used herein, refers to an alkyl group comprising a cyclic alkane moiety containing from, for example, 3 to 6 carbon atoms or from 5 to 6 carbon atoms which contains at least 1 heteroatom (e.g., O, S, N, and/or P) in the core of the molecule (i.e., any part of the molecule except for the alkane-containing portion). Accordingly, at least 1 heteroatom can be a pendant substituent or encompassed in a cyclic chain. In certain instances, the heterocycloalkyl has at least 2 heteroatoms in the core of the molecule (e.g., at least 3, 4, 5, or 6 heteroatoms in the core of the molecule). In some embodiments, the heterocycloalkyl group comprises a moiety selected from an ether, an ester, a carbonate, an amide, an amine, a carbamate, a thioether, a thioester, a phosphate, a haloalkane, an acetyl, an alcohol, a ketone, an aldehyde, a carboxylate, a carboxylic acid, a hemiacetal, an acetal, a ketal, an imine, and imide, a thiol, a disulfide, a sulfoxide, a thioketone, or a combination thereof An exemplary, but non-limiting list of heterocycloalkyl groups includes tetrahydrofuranyl, piperazinyl, morpholinyl, cyclohexanonyl, and 2-cyclohexylethanolyl.

As used herein, "aryl group" refers to any suitable substituted or unsubstituted aromatic or heteroaromatic group, as described herein. In some embodiments of the non-oxidizable liquid, the aryl group is deactivated, which means the aryl group is substituted with at least 1 electron withdrawing substituent, for example, at least 2, 3, or 4 electron withdrawing substituents, such as those described herein.

In some embodiments, the sulfone is a non-oxidizable liquid that contains a sulfonyl (—$SO_2$) functional group, such as (methylsulfonyl)benzene, (ethylsulfonyl)benzene, (propylsulfonyl)benzene, (isopropylsulfonyl)benzene, (butylsulfonyl)benzene, (methylsulfonyl)pyridine, (ethylsulfonyl)pyridine, (propylsulfonyl)pyridne, (isopropylsulfonyl) pyridine, (butylsulfonyl)pyridine, (cyclohexylsulfonyl) benzene, sulfonyldibenzene, dibenzothiophene 5,5-dioxide, 2,3-dihydrobenzothiophene 1,1-dioxide, or thiochromane 1,1-dioxide, each of which is substituted or unsubstituted.

In some embodiments, the sulfone is (methylsulfonyl) methane ("dimethyl sulfone"), (methylsulfonyl)ethane, tetrahydrothiophene 1,1-dioxide ("sulfolane"), tetrahydro-2H-thiopyran 1,1-dioxide, thietane 1,1-dioxide, (ethylsulfonyl) ethane, 1-(ethylsulfonyl)propane, 1-(propylsulfonyl) propane, 1-(propylsulfonyl)butane, 1-(butylsulfonyl)butane, 2-(ethylsulfonyl)propane, 2-(isopropylsulfonyl)propane, 1-(ethylsulfonyl)-2-methylpropane, 1-(methylsulfonyl)butane, 1-(ethylsulfonyl)butane, 1-(isopropylsulfonyl)-2-methylpropane, 1-(ethylsulfonyl)-2-methylpropane, 2-methyl-1-(methylsulfonyl)propane, 1-(isobutylsulfonyl)-2-methylpropane, 2-(tert-butylsulfonyl)-2-methylpropane, perfluorinated (methylsulfonyl)methane, perfluorinated (methylsulfonyl)ethane, perfluorinated tetrahydrothiophene 1,1-dioxide, perfluorinated tetrahydro-2H-thiopyran 1,1-dioxide, perfluorinated thietane 1,1-dioxide, perfluorinated (ethylsulfonyl)ethane, perfluorinated 1-(ethylsulfonyl)propane, perfluorinated 1-(propylsulfonyl)propane, perfluorinated 1-(propylsulfonyl)butane, perfluorinated 1-(butylsulfonyl)butane, perfluorinated 2-(ethylsulfonyl)propane, perfluorinated 2-(isopropylsulfonyl)propane, perfluorinated 1-(ethylsulfonyl)-2-methylpropane, perfluorinated 1-(methylsulfonyl)butane, perfluorinated 1-(ethylsulfonyl)butane, perfluorinated 1-(isopropylsulfonyl)-2-methylpropane, perfluorinated 1-(ethylsulfonyl)-2-methylpropane, perfluorinated 2-methyl-1-(methylsulfonyl)propane, perfluorinated 1-(isobutylsulfonyl)-2-methylpropane, or perfluorinated 2-(tert-butylsulfonyl)-2-methylpropane, each of which is substituted or unsubstituted.

In other embodiments, the sulfone is (methylsulfonyl) methane ("dimethyl sulfone"), (methylsulfonyl)ethane, tetrahydrothiophene 1,1-dioxide ("sulfolane"), tetrahydro-2H-thiopyran 1,1-dioxide, thietane 1,1-dioxide, perfluorinated (methylsulfonyl)methane, perfluorinated (methylsulfonyl)ethane, perfluorinated tetrahydrothiophene 1,1-dioxide, perfluorinated tetrahydro-2H-thiopyran 1,1-dioxide, or perfluorinated thietane 1,1-dioxide.

In some embodiments, the non-oxidizable liquid is one or more deactivated arene(s). As used herein, "deactivated arene" refers to at least one monocyclic or polycyclic aromatic compound, as described herein, that has 1 or more electron withdrawing substituents. In some embodiments, the arene compound has 2 or more electron withdrawing substituents, for example, 3 or more, 4 or more, 5 or more, or 6 or more electron withdrawing substituents. In some embodiments, each carbon of the deactivated arene has at least one electron withdrawing substituent. In certain embodiments, the deactivated arene is polycyclic and has 2, 3, or 4 aromatic rings and includes, e.g., benzene, toluene, xylene, naphthalene, biphenyl, and anthracene. The electron withdrawing substituent can be any suitable electron withdrawing substituent, such as those described herein.

An exemplary, but non-limiting list of deactivated arenes, such as deactivated benzenes, includes $C_6H_5(NO_2)$, $C_6H_5(CF_3)$, $C_6H_5F$, $C_6H_5(COOH)$, $C_6H_5(CONH_2)$, $C_6H_5(COOCF_3)$, $C_6H_5(OOCCF_3)$, $C_6H_5(CN)$, $C_6H_5(SO_3H)$, $C_6H_5(SO_3R)$, $C_6H_5(SO_3Q)$, m-$C6H_4(NO_2)_2$, o-$C_6H_4(NO_2)_2$, p-$C_6H_4(NO_2)_2$, m-$C_6H_4(CF_3)_2$, o-$C_6H_4(CF_3)_2$, p-$C_6H_4(CF_3)_2$, m-$C_6H_4F_2$, o-$C_6H_4F_2$, p-$C_6H_4F_2$, m-$C_6H_4(COOH)_2$, o-$C_6H_4(COOH)_2$, p-$C_6H_4(COOH)_2$, m-$C_6H_4(CONH_2)_2$, o-$C_6H_4(CONH_2)_2$, p-$C_6H_4(CONH_2)_2$, m-$C_6H_4(COOCF_3)_2$, o-$C_6H_4(COOCF_3)_2$, p-$C_6H_4(COOCF_3)_2$, m-C$_6$H$_4$(OOCCF$_3$)$_2$, o-C$_6$H$_4$(OOCCF$_3$)$_2$, p-C$_6$H$_4$(OOCCF$_3$)$_2$, m-C$_6$H$_4$(CN)$_2$, o-C$_6$H$_4$(CN)$_2$, p-C$_6$H$_4$(CN)$_2$, m-C$_6$H$_4$(SO$_3$H)$_2$, o-C$_6$H$_4$(SO$_3$H)$_2$, p-C$_6$H$_4$(SO$_3$H)$_2$, m-C$_6$H$_4$(SO$_3$R)$_2$, o-C$_6$H$_4$(SO$_3$R)$_2$, p-C$_6$H$_4$(SO$_3$R)$_2$, m-C$_6$H$_4$(SO$_3$Q)$_2$, o-C$_6$H$_4$(SO$_3$Q)$_2$, p-C$_6$H$_4$(SO$_3$Q)$_2$, m-C$_6$H$_4$(CF$_3$)(NO$_2$), o-C$_6$H$_4$(CF$_3$)(NO$_2$), p-C$_6$H$_4$(CF$_3$)(NO$_2$), m-C$_6$H$_4$(CF$_3$)(F), o-C$_6$H$_4$(CF$_3$)(F), p-C$_6$H$_4$(CF$_3$)(F), m-C$_6$H$_4$(CF$_3$)(COOH), o-C$_6$H$_4$(CF$_3$)(COOH), p-C$_6$H$_4$(CF$_3$)(COOH), m-C$_6$H$_4$(CF$_3$)(CONH$_2$), o-C$_6$H$_4$(CF$_3$)(CONH$_2$), p-C$_6$H$_4$(CF$_3$)(CONH$_2$), m-C$_6$H$_4$(CF$_3$)(CN), o-C$_6$H$_4$(CF$_3$)(CN), p-C$_6$H$_4$(CF$_3$)(CN), m-C$_6$H$_4$(CF$_3$)(SO$_3$H), o-C$_6$H$_4$(CF$_3$)(SO$_3$H), p-C$_6$H$_4$(CF$_3$)(SO$_3$H), m-C$_6$H$_4$(CF$_3$)(SO$_3$R), o-C$_6$H$_4$(CF$_3$)(SO$_3$R), p-C$_6$H$_4$(CF$_3$)(SO$_3$R), m-C$_6$H$_4$(CF$_3$)(SO$_3$Q), o-C$_6$H$_4$(CF$_3$)(SO$_3$Q), p-C$_6$H$_4$(CF$_3$)(SO$_3$Q), m-C$_6$H$_4$(F)(NO$_2$), o-C$_6$H$_4$(F)(NO$_2$), p-C$_6$H$_4$(F)(NO$_2$), m-C$_6$H$_4$(COOH)(NO$_2$), o-C$_6$H$_4$(COOH)(NO$_2$), p-C$_6$H$_4$(COOH)(NO$_2$), m-C$_6$H$_4$(CONH$_2$)(NO$_2$), o-C$_6$H$_4$(CONH$_2$)(NO$_2$), p-C$_6$H$_4$(CONH$_2$)(NO$_2$), m-C$_6$H$_4$(COOCF$_3$)(NO$_2$), o-C$_6$H$_4$(COOCF$_3$)(NO$_2$), p-C$_6$H$_4$(COOCF$_3$)(NO$_2$), m-C$_6$H$_4$(OOCCF$_3$)(NO$_2$), o-C$_6$H$_4$(OOCCF$_3$)(NO$_2$), p-C$_6$H$_4$(OOCCF$_3$)(NO$_2$), m-C$_6$H$_4$(CN)(NO$_2$), o-C$_6$H$_4$(CN)(NO$_2$), p-C$_6$H$_4$(CN)(NO$_2$), m-C$_6$H$_4$(SO$_3$H)(NO$_2$), o-C$_6$H$_4$(SO$_3$H)(NO$_2$), p-C$_6$H$_4$(SO$_3$H)(NO$_2$), m-C$_6$H$_4$(SO$_3$R)(NO$_2$), o-C$_6$H$_4$(SO$_3$R)(NO$_2$), p-C$_6$H$_4$(SO$_3$R)(NO$_2$), m-C$_6$H$_4$(SO$_3$Q)(NO$_2$), o-C$_6$H$_4$(SO$_3$Q)(NO$_2$), p-C$_6$H$_4$(SO$_3$Q)(NO$_2$), 1,2,3-C$_6$H$_3$(CF$_3$)$_2$(NO$_2$), 1,3,4-C$_6$H$_3$(CF$_3$)$_2$(NO$_2$), 1,3,5-C$_6$H$_3$(CF$_3$)$_2$(NO$_2$), 1,2,3-C$_6$H$_3$(CF$_3$)(NO$_2$)$_2$, 1,3,4-C$_6$H$_3$(CF$_3$)(NO$_2$)$_2$, 1,3,5-C$_6$H$_3$(CF$_3$)(NO$_2$)$_2$, 1,2,3-C$_6$H$_3$F$_2$(NO$_2$), 1,3,4-C$_6$H$_3$F$_2$(NO$_2$), 1,3,5-C$_6$H$_3$F$_2$(NO$_2$), 1,2,3-C$_6$H$_3$(CF$_3$)F$_2$, 1,3,4-C$_6$H$_3$(CF$_3$)F$_2$, 1,3,5-C$_6$H$_3$(CF$_3$)F$_2$, 1,2,3-C$_6$H$_3$(COOH)$_2$(NO$_2$), 1,3,4-C$_6$H$_3$(COOH)$_2$(NO$_2$), 1,3,5-C$_6$H$_3$(COOH)$_2$(NO$_2$), 1,2,3-C$_6$H$_3$(CF$_3$)(COOH)$_2$, 1,3,4-C$_6$H$_3$(CF$_3$)(COOH)$_2$, 1,3,5-C$_6$H$_3$(CF$_3$)(COOH)$_2$, 1,2,3-C$_6$H$_3$(CONH$_2$)$_2$(NO$_2$), 1,3,4-C$_6$H$_3$(CONH$_2$)$_2$(NO$_2$), 1,3,5-C$_6$H$_3$(CONH$_2$)$_2$(NO$_2$), 1,2,3-C$_6$H$_3$(CF$_3$)(CONH$_2$)$_2$, 1,3,4-C$_6$H$_3$(CF$_3$)(CONH$_2$)$_2$, 1,3,5-C$_6$H$_3$(CF$_3$)(CONH$_2$)$_2$, 1,2,3-C$_6$H$_3$(COOCF$_3$)$_2$(NO$_2$), 1,3,4-C$_6$H$_3$(COOCF$_3$)$_2$(NO$_2$), 1,3,5-C$_6$H$_3$(COOCF$_3$)$_2$(NO$_2$), 1,2,3-C$_6$H$_3$(CF$_3$)(COOCF$_3$)$_2$, 1,3,4-C$_6$H$_3$(CF$_3$)(COOCF$_3$)$_2$, 1,3,5-C$_6$H$_3$(CF$_3$)(COOCF$_3$)$_2$, 1,2,3-C$_6$H$_3$(OOCCF$_3$)$_2$(NO$_2$), 1,3,4-C$_6$H$_3$(OOCCF$_3$)$_2$(NO$_2$), 1,3,5-C$_6$H$_3$(OOCCF$_3$)$_2$(NO$_2$), 1,2,3-C$_6$H$_3$(CF$_3$)(OOCCF$_3$)$_2$, 1,3,4-C$_6$H$_3$(CF$_3$)(OOCCF$_3$)$_2$, 1,3,5-C6H$_3$(CF$_3$)(OOCCF$_3$)$_2$, 1,2,3-C$_6$H$_3$(CN)$_2$(NO$_2$), 1,3,4-C$_6$H$_3$(CN)$_2$(NO$_2$), 1,3,5-C$_6$H$_3$(CN)$_2$(NO$_2$), 1,2,3-C$_6$H$_3$(SO$_3$H)(CN)$_2$, 1,3,4-C$_6$H$_3$(SO$_3$H)(CN)$_2$, 1,3,5-C$_6$H$_3$(SO$_3$H)(CN)$_2$, 1,2,3-C$_6$H$_3$(SO$_3$R)(CN)$_2$, 1,3,4-C$_6$H$_3$(SO$_3$R)(CN)$_2$, 1,3,5-C$_6$H$_3$(SO$_3$R)(CN)$_2$, 1,2,3-C$_6$H$_3$(SO$_3$Q)(CN)$_2$, 1,3,4-C$_6$H$_3$(SO$_3$Q)(CN)$_2$, 1,3,5-C$_6$H$_3$(SO$_3$Q)(CN)$_2$, 1,2,3-C$_6$H$_3$(CF$_3$)$_2$(SO$_3$H), 1,3,4-C$_6$H$_3$(CF$_3$)$_2$(SO$_3$H), 1,3,5-C$_6$H$_3$(CF$_3$)$_2$(SO$_3$H), 1,2,3-C$_6$H$_3$(CF$_3$)$_2$(SO$_3$R), 1,3,4-C$_6$H$_3$(CF$_3$)$_2$(SO$_3$R), 1,3,5-C$_6$H$_3$(CF$_3$)$_2$(SO$_3$R), 1,2,3-C$_6$H$_3$(CF$_3$)$_2$(SO$_3$Q), 1,3,4-C$_6$H$_3$(CF$_3$)$_2$(SO$_3$Q), 1,3,5-C$_6$H$_3$(CF$_3$)$_2$(SO$_3$Q), 1,2,3-C$_6$H$_3$(CF$_3$)$_3$, 1,3,4-C$_6$H$_3$(CF$_3$)$_3$, 1,3,5-C$_6$H$_3$(CF$_3$)$_3$, 1,2,3-C$_6$H$_3$(NO$_2$)$_3$, 1,3,4-C$_6$H$_3$(NO$_2$)$_3$, 1,3,5-C$_6$H$_3$(NO$_2$)$_3$, 1,2,3-C$_6$H$_3$F$_3$, 1,3,4-C$_6$H$_3$F$_3$, 1,3,5-C$_6$H$_3$F$_3$, 1,2,3-C$_6$H$_3$(COOH)$_3$, 1,3,4-C$_6$H$_3$(COOH)$_3$, 1,3,5-C$_6$H$_3$(COOH)$_3$, 1,2,3-C$_6$H$_3$(COOCF$_3$)$_3$, 1,3,4-C$_6$H$_3$(COOCF$_3$)$_3$, 1,3,5-C$_6$H$_3$(COOCF$_3$)$_3$, 1,2,3-C$_6$H$_3$(OOCCF$_3$)$_3$, 1,3,4-C$_6$H$_3$(OOCCF$_3$)$_3$, 1,3,5-C$_6$H$_3$(OOCCF$_3$)$_3$, 1,2,3-C$_6$H$_3$(CN)$_3$, 1,3,4-C$_6$H$_3$(CN)$_3$, 1,3,5-C$_6$H$_3$(CN)$_3$, 1,2,3-C$_6$H$_3$(SO$_3$H)$_3$, 1,3,4-C$_6$H$_3$(SO$_3$H)$_3$, 1,3,5-C$_6$H$_3$(SO$_3$H)$_3$, 1,2,3-C$_6$H$_3$(SO$_3$R)$_3$, 1,3,4-C$_6$H$_3$(SO$_3$R)$_3$, 1,3,5-C$_6$H$_3$(SO$_3$R)$_3$, 1,2,3-C$_6$H$_3$(SO$_3$Q)$_3$, 1,3,4-C$_6$H$_3$(SO$_3$Q)$_3$, 1,3,5-C$_6$H$_3$(SO$_3$Q)$_3$, 1,2,3-C$_6$H$_3$(CONH$_2$)$_3$, 1,3,4-C$_6$H3(CONH$_2$)$_3$, and 1,3,5-C$_6$H$_3$(CONH$_2$)$_3$. As used herein, R is any aliphatic (e.g., C$_{1-8}$ alkyl, fluoro-C$_{1-8}$ alkyl), heteroaliphatic, aromatic, or heteroaromatic moiety, each of which is optionally substituted, and Q refers to a cation.

In certain embodiments, the non-oxidizable liquid is a nitroarene. As used herein, "nitroarene" refers to any deactivated arene comprising at least one nitro group. For example, the nitroarene can be nitro-substituted benzene, nitro-substituted toluene, nitro-substituted xylene, nitro-substituted naphthalene, nitro-substituted biphenyl, or nitro-substituted anthracene.

In some embodiments, the non-oxidizable liquid is one or more deactivated aliphatic(s). As used herein, "deactivated aliphatic" refers to at least one aliphatic group, as described herein, that has 1 or more electron withdrawing substituents (e.g., 2 or more, 3 or more, 4 or more, or 5 or more electron withdrawing substituents).

In some embodiments, the deactivated aliphatic non-oxidizable liquid is at least one saturated, unsaturated, branched, straight-chained, or cyclic C$_1$-C$_9$ alkyl aliphatic group that is substituted with at least 1 electron withdrawing substituent (e.g., 2 or more, 3 or more, 4 or more, or 5 or more electron withdrawing substituents). An exemplary, but non-limiting list of deactivated C$_1$-C$_9$ alkyl aliphatics is methyl, ethyl, n-propyl, iso-propyl, n-butyl, sec-butyl, tert-butyl, n-pentyl, sec-pentyl, neo-pentyl, hexyl, heptyl, octyl, nonyl, cyclopentyl, cyclohexyl, propenyl, 2-butenyl, 3-butenyl, 2-pentenyl, 3-pentenyl, 4-pentenyl, or a combination thereof, in which the C$_1$-C$_9$ alkyl is substituted with 1 or more electron withdrawing substituents, such those described herein.

In some instances, the deactivated aliphatic is methyl, ethyl, n-propyl, iso-propyl, n-butyl, sec-butyl, tert-butyl, n-pentyl, sec-pentyl, or neo-pentyl, in which the methyl, ethyl, n-propyl, iso-propyl, n-butyl, sec-butyl, tert-butyl, n-pentyl, sec-pentyl, or neo-pentyl is substituted with 1 or more electron withdrawing substituents. In certain embodiments, the deactivated aliphatic is methyl, ethyl, n-propyl, or iso-propyl in which the methyl, ethyl, n-propane, or iso-propyl is substituted with 1 or more electron withdrawing substituents, such those described herein.

In other embodiments, the deactivated aliphatic is trifluoromethanol, trifluoromethyl 2,2,2-trifluoroacetate, 2,2,2-trifluoroethan-1-ol, 2,2,2-trifluoroethyl 2,2,2-trifluoroacetate, perfluoroethyl 2,2,2-trifluoroacetate, 1,1,2,2,2-pentafluoroethan-1-ol, nitromethane, trifluoro(nitro)methane, 1,1,2,2-tetrafluoroethane-1,2-diol, 1,1,2,2-tetrafluoro-2-hydroxyethyl 2,2,2-trifluoroacetate, perfluoroethane-1,2-diyl bis(2,2,2-trifluoroacetate), ethane-1,2-diyl bis(2,2,2-trifluoroacetate), 1,1,2,2,3,3-hexafluoropropane-1,3-diol, propane-1,2,3-triyl tris(2,2,2-trifluoroacetate), oxalic acid, 1,1,1,4,4,4-hexafluorobutane-2,3-dione, methyl 2,2,2-trifluoroacetate, methyl 2,2,3,3,3-pentafluoropropanoate, or trifluoromethyl 2,2,3,3,3-pentafluoropropanoate.

In other embodiments, the deactivated aliphatic is trifluoromethyl acetate, 1,1-difluoroethyl acetate, 2,2,2-trifluoroethyl acetate, perfluoroethyl acetate, perfluoropropan-2-yl acetate, 1,1,1,3,3,3-hexafluoropropan-2-yl acetate, 1,1,2,2-tetrafluoro-2-hydroxyethyl acetate, perfluoroethane-1,2-diyl diacetate, ethane-1,2-diyl diacetate, propane-1,2,3-triyl trisacetate, perfluoropropane-1,2,3-triyl triacetate, 1,1,3,3-tetrafluoropropane-1,2,3-triyl triacetate, or 1,1-difluoroethane-1,2-diyl diacetate.

In some embodiments, the non-oxidizable liquid is one or more deactivated heteroarene(s). As used herein, "deactivated heteroarene" refers to at least one monocyclic or polycylic heteroaromatic compound which has at least one heteroatom (O, S, or N) in at least one of the rings. The term "heteroaromatic" is as described herein.

In some embodiments, the deactivated heteroarene is isoxazole, oxazole, isothiazole, thiazole, imidazole, thiadiazole, tetrazole, triazole, oxadiazole, pyrazole, pyrazine, pyrimidine, or triazine, each of which is substituted or unsubstituted. In other preferred embodiments, the deactivated heteroarene is pyrrole, furan, thiophene, or pyridine, each of which is substituted with at least one substituent that is an electron withdrawing substituent.

In other embodiments, the deactivated heteroarene is perfluoroisoxazole, perfluorooxazole, perfluoroisothiazole, perfluorothiazole, perfluoroimidazole, perfluorothiadiazole, perfluorotetrazole, perfluorotriazole, perfluorooxadiazole, perfluoropyrazole, perfluoropyrazine, perfluorotriazine, perfluoropyrrole, perfluorofuran, perfluorothiophene, perfluoropyridine, nitropyrrole, nitrofuran, nitrothiophene, nitropyridine, cyanopyrrole, cyanofuran, cyanothiophene, cyanopyridine, picolinic acid, nicotinic acid, isonicotinic acid, pyridine sulfonic acid, pyrrole sulfonic acid, furan sulfonic acid, thiophene sulfonic acid, pyridine carboxylic acid, pyrrole carboxylic acid, furan carboxylic acid, thiophene carboxylic acid, trifluoromethyl pyridine, trifluoromethyl pyrrole, trifluoromethyl furan, or trifluoromethyl thiophene.

In some embodiments, the non-oxidizable liquid is one or more deactivated heteroaliphatic(s). The term "heteroaliphatic" is as described herein. In some embodiments, the heteroaliphatic compound is an ether, an ester, a carbonate, an amide, an amine, a carbamate, a thioether, a thioester, a phosphate, or a heterocycloalkane. The term "heterocycloalkane" refers to a cycloalkane, as described herein, in which at least one heteroatom (e.g., O, S, N, and/or P) replaces at least one carbon in the ring system. In an aspect, a heterocycloalkane is a 5-, 6-, or 7-membered monocyclic ring and contains one, two, or three heteroatoms selected from nitrogen, oxygen, and sulfur. Examples of such heterocycloalkane rings are pyrrolidine, pyrroline, pyran, piperidine, quinuclidine, imidazoline, dioxane, dioxolane, morpholine, thiomorpholine, trithiane, dithiane, pyrazoline, pyrazolidine, piperazine, or a combination thereof.

In certain embodiments, the deactivated heteroaliphatic has at least 1 electron withdrawing substituent. In some embodiments, the deactivated heteroaliphatic has at least 2 electron withdrawing substituents (e.g., at least 3, 4, 5, or 6 electron withdrawing substituents), such as those described herein.

In other embodiments, the deactivated heteroaliphatic compound is trifluoro(trifluoromethoxy)methane, 1,1,1,2,2-pentafluoro-2-(trifluoromethoxy)ethane, 1,1,1,2,2-pentafluoro-2-(perfluoroethoxy)ethane, tris(trifluoromethyl)amine, 1,1,2,2,2-pentafluoro-N-(perfluoroethyl)-N-(trifluoromethyl)ethan-1-amine, tris(perfluoroethyl)amine, 2,2,2-trifluoro-N,N-bis(trifluoromethyl)acetamide, N,N-bis(trifluoromethyl)formamide, 2,2,2-trifluoroacetamide, perfluoropyrrolidine, perfluoropyrroline, perfluoropyran, perfluoropiperidine, perfluorodioxane, perfluoromorpholine, perfluoropiperazine, nitropyrrolidine, nitropyrroline, nitropyran, nitropiperidine, nitrodioxane, nitromorpholine, nitropiperazine, cyanopyrrolidine, cyanopyrroline, cyanopyran, cyanopiperidine, cyanodioxane, cyanomorpholine, cyanopiperazine, pyrrolidine carboxylic acid, pyrroline carboxylic acid, pyran carboxylic acid, piperidine carboxylic acid, dioxane carboxylic acid, morpholine carboxylic acid, piperazine carboxylic acid, pyrrolidine sulfonic acid, pyrroline sulfonic acid, pyran sulfonic acid, piperidine sulfonic acid, dioxane sulfonic acid, morpholine sulfonic acid, or piperazine sulfonic acid.

In some embodiments, the non-oxidizable liquid is one or more carbonate(s). The carbonate can be chemical compound comprising at least one carbonate moiety (e.g., 1 carbonate, 2 carbonates, 3 carbonates, or 4 carbonates). For example, the carbonate can be an alkyl carbonate, a heteroalkyl carbonate, a cycloalkyl carbonate, a heterocycloalkyl carbonate, an aryl carbonate, hydrogen carbonate, or a combination thereof.

In any of the embodiments described herein, the electron withdrawing substituent can be any suitable electron withdrawing group, such as —NO$_2$, fluoro-C$_{1-8}$ alkyl, —F, —OOCR, —COOH, —H$_2^+$, —CONH$_2$, —COOR, —NR$_3^+$, —CN, —SO$_3$H, —SO$_3$R, —SO$_3$W, or a combination thereof, in which R is hydrogen or any aliphatic (e.g., C$_{1-8}$ alkyl, fluoro-C$_{1-8}$ alkyl), heteroaliphatic, aromatic, or heteroaromatic moiety, each of which is optionally substituted, and W is a cation comprising a metal selected from boron, bismuth, antimony, arsenic, lanthanum, cerium, scandium, yttrium, titanium, zirconium, hafnium, silver, zinc, cadmium, aluminum, gallium, indium, germanium, tin, phosphorus, an alkali metal, or an alkaline earth metal. In certain embodiments, R is —CF$_3$.

In some embodiments, the non-oxidizable liquid is the same as a product of the reaction described herein. For example, the non-oxidizable liquid can be the oxidized intermediate (e.g., a product of the oxidation of propane can be 1,2-propane(trifluoroacetate), which is a deactivated heteroaliphatic).

In some embodiments, the liquid medium comprises a salt additive.

Generally, the salt additive is one or more compounds of the formula Q$_a$Z$_b$, in which Q is a cation, Z is a bridging oxide, a terminal oxide, a hydroxide, or an anion of the oxygen acid, a is an integer from 1 to 5 (i.e., 1, 2, 3, 4, or 5), b is an integer from 1 to 5 (i.e., 1, 2, 3, 4, or 5), and wherein a and b are the same or different and balance the oxidation states of Q and Z.

Q can be any suitable cation in any suitable oxidation state. In some embodiments, Q can be a proton, ammonium, a cation of an alkali metal, a cation of an alkaline earth metal, a cation of a rare-earth metal, a main group element cation, or a combination thereof. In some embodiments, Q is hydrogen or a cation of lithium, sodium, potassium, rubidium, cesium, francium, beryllium, magnesium, calcium, strontium, barium, or radium. Typically, Q has an oxidation state of +5, +4, +3, +2, or +1.

Z can be any suitable oxide (e.g., a bridging oxide or a terminal oxide), hydroxide, or anion of the oxygen acid, as described herein, in any suitable oxidation state. In some embodiments, Z is an anion of the oxygen acid that is one or more selected from an aliphatic carboxylate, heteroaliphatic carboxylate, aromatic carboxylate, heteroaromatic carboxylate, aliphatic sulfonate, heteroaliphatic sulfonate, aromatic sulfonate, heteroaromatic sulfonate, aliphatic phosphate, heteroaliphatic phosphate, aromatic phosphate, heteroaromatic phosphate, aliphatic borate, heteroaliphatic borate, aromatic borate, and heteroaromatic borate. In certain embodiments, Z is selected from a bridging oxide, a terminal oxide, hydroxide, sulfite, sulfate, hydrogen sulfate, thiosulfate, nitrite, nitrate, phosphite, phosphate, hydrogen phosphate, dihydrogen phosphate, carbonate, hydrogen carbonate, oxalate, cyanate, isocyanate, thiocyanate, carboxylate, sulfonate, and a combination thereof As used herein, carboxylates can be alkylated variants (e.g., acetate), fluorinated variants (e.g., trifluoroacetate), or arylated variants (e.g., benzoates or benzoic acids). As used herein, "alkylated variants" and "arylated variants" refer to a carboxylic acid containing an alkyl group or an aryl group, respectively, as defined herein. Similarly, sulfonates can be alkylated variants (e.g., methanesulfonate) or fluorinated variants (e.g., trifluoromethanesulfonate). In certain embodiments, Z is one or more selected from trifluoroacetate, acetate, benzoate, sulfate, methanesulfonate, and trifluoromethanesulfonate. Typically, Z has an oxidation state of −4, −3, −2, or −1.

The oxygen acid in the context of the oxidizing electrophile and the oxygen acid in the context of the additive are each independently chosen. Accordingly, the oxygen acid in the context of the oxidizing electrophile and the oxygen acid in the context of the additive can be the same or different. Typically, the oxygen acid in the context of the oxidizing electrophile and the oxygen acid in the context of the additive are the same.

In preferred embodiments, the liquid medium and/or oxidizing composition comprises a salt of the oxygen acid.

In certain embodiments, X of the oxidizing electrophile formula $M^{+n}X_pL_q$ and Z of the additive are the same.

In certain embodiments, X of the oxidizing electrophile formula $M^{+n}X_pL_q$ and Z of the additive are different.

In some embodiments, $Q_aZ_b$ is a Brøsted acid, a salt, or a combination thereof In some instances, $Q_aZ_b$ is one or more of acetic acid, ammonium acetate, lithium acetate, sodium acetate, potassium acetate, rubidium acetate, cesium acetate, francium acetate, beryllium acetate, magnesium acetate, calcium acetate, strontium acetate, barium acetate, radium acetate, benzoic acid, ammonium benzoate, lithium benzoate, sodium, potassium benzoate, rubidium benzoate, cesium benzoate, francium benzoate, beryllium benzoate, magnesium benzoate, calcium benzoate, strontium benzoate, barium benzoate, radium benzoate, trifluoroacetic acid, ammonium trifluoroacetate, lithium trifluoroacetate, sodium trifluoroacetate, potassium trifluoroacetate, trifluoroacetic acid, ammonium trifluoroacetate, lithium trifluoroacetate, sodium trifluoroacetate, potassium trifluoroacetate, rubidium trifluoroacetate, cesium trifluoroacetate, francium trifluoroacetate, beryllium trifluoroacetate, magnesium trifluoroacetate, calcium trifluoroacetate, strontium trifluoroacetate, barium trifluoroacetate, radium trifluoroacetate, sulfuric acid, ammonium sulfate, lithium sulfate, sodium sulfate, potassium sulfate, rubidium sulfate, cesium sulfate, francium sulfate, beryllium sulfate, magnesium sulfate, calcium sulfate, strontium sulfate, barium sulfate, radium sulfate, phosphoric acid, methanesulfonic acid, ammonium methanesulfonate, lithium methanesulfonate, sodium methanesulfonate, potassium methanesulfonate, rubidium methanesulfonate, cesium methanesulfonate, francium methanesulfonate, beryllium methanesulfonate, magnesium methanesulfonate, calcium methanesulfonate, strontium methanesulfonate, barium methanesulfonate, radium methanesulfonate, trifluoromethanesulfonic acid, ammonium trifluoromethanesulfonate, lithium trifluoromethanesulfonate, sodium trifluoromethanesulfonate, potassium trifluoromethanesulfonate, rubidium trifluoromethanesulfonate, cesium trifluoromethanesulfonate, francium trifluoromethanesulfonate, beryllium trifluoromethanesulfonate, magnesium trifluoromethanesulfonate, calcium trifluoromethanesulfonate, strontium trifluoromethanesulfonate, barium trifluoromethanesulfonate, or radium trifluoromethanesulfonate. In preferred embodiments, $Q_aZ_b$ is trifluoroacetic acid, acetic acid, benzoic acid, methanesulfonic acid, or a combination thereof, each of which can be substituted or unsubstituted.

In some embodiments, the liquid medium and/or oxidizing composition comprises a Lewis Acid. Generally, the Lewis acid is of formula $Q_aZ_b$, wherein $Q_aZ_b$ is any suitable, non-halide containing Lewis acid, which is a strong electron pair acceptor. In embodiments where $Q_aZ_b$ is a non-halide containing Lewis acid, Q can be a cation of a transition metal, a cation of a rare-earth metal, a main group cation, or a combination thereof In some embodiments, Q is a cation of boron, bismuth, antimony, arsenic, lanthanum, cerium, scandium, yttrium, titanium, zirconium, hafnium, silver, zinc, cadmium, aluminum, gallium, indium, germanium, tin, phosphorus, or a combination thereof Typically, Q has an oxidation state of +5, +4, +3, +2, or +1. In certain embodiments, Q is In(III), Sc(III), Zn(II), Ti(IV), Al(III), Ga(III), B(III), Sb(III), Bi(III), or As(III). It will be understood that any one or more Q(s) can be combined with any one or more Z(s), such that fundamental chemical rules are satisfied, to form the non-halide containing Lewis acid (e.g., Ce(OAc)$_3$, Ce(OTf)$_3$, Zn(OAc)$_2$, Zn(OTf)$_2$, ZnO, In(OAc)$_3$, In(OTf)$_3$, In$_2$O$_3$, Sb(OAc)$_3$, Sb(OTf)$_3$, Sb$_2$O$_3$, Bi(OAc)$_3$, Bi(OTf)$_3$, Bi$_2$O$_3$, Al(OTf)$_3$, Ga(OTf)$_3$, Sc(OAc)$_3$, Sc(OTf)$_3$, or Sc(OMs)$_3$). As used herein, "OTf" refers to trifluoromethanesulfonate, "OMs" refers to mesylate, and "OAc" refers to acetate.

In some embodiments, the liquid medium does not contain a halide ion (e.g., Cl$^−$, Br$^−$, I$^−$). or As used herein, the term "halide ion" is considered different from the term halogen atom. In particular, the term halide ion does not encompass a halogen atom (e.g., a fluorine atom, a chlorine atom, a bromine atom, or an iodine atom) attached to an aliphatic or aromatic substituent (i.e., a substituent that will not decompose to form free ions under reaction conditions). For example, iodine can be present in aromatic-iodine species, as this form of iodine would not be considered a halide ion. Instead, the term "halide ion" refers to ions of salt additives, such as alkali halide compounds (e.g., NaI, KCl, etc.). Accordingly, the halide ion can be present in the liquid medium in an amount less than 0.1 mol % (e.g., less than 0.05 mol %, less than 0.01 mol %, less than 0.005 mol %, less than 0.001 mol %) or about 0 mol % of the main group element.

In some embodiments, the liquid medium comprises a trace amount of a halide ion (e.g., Cl$^−$, Br$^−$, I$^−$, or a combination thereof). It is possible that impurities in starting materials or from reactor corrosion can be responsible for the presence of trace halide ions. Accordingly, the halide ion can be present in an amount of about 0.00001 mol % of the main group element or more (e.g., about 0.0001 mol % or more, about 0.001 mol % or more, 0.01 mol % or more, 0.1 mol % or more, or about 1 mol % or more). Alternatively, or in addition, the halide ion can be present in an amount of about 5 mol % of the main group element or less (e.g., about 4 mol % or less, about 3 mol % or less, about 2 mol % or less, about 1 mol % or less, or about 0.1 mol % or less). Any two of the foregoing endpoints can be used to define a close-ended range, or any single endpoint can be used alone to define an open-ended range.

In some embodiments, the additive is water.

In some embodiments, the process comprises separating one or more components from the liquid medium. The one or more components can be separated by any suitable means, such as by filtration, distillation, flashing, rectifying, stripping, evaporation, absorption, adsorption, column chromatography, crystallization, centrifugation, extraction, recrystallization, membrane separation, or any combination thereof Distillation can be used to separate components of the liquid medium based on differences in the volatilities of the mixture components. A distillation process may optionally include a chemical reaction. An example of distillation is the removal of water and glycol products from a mixture of higher boiling components including an oxidizing electrophile in solution.

Flashing can be used to remove one or more light components from the liquid medium. Flashing is the partial vaporization that occurs when the pressure of a liquid stream is reduced. A typical flashing process includes a flow restriction such as a control valve followed by a vessel (i.e. flash drum) to allow for de-entrainment of liquid from a gas stream. Additional heating or cooling is optional. A flashing operation can be combined with chemical reactions. Upon flashing, the vapor phase is richer in the more volatile components compared to the remaining liquid phase. An adiabatic flashing process results in lower temperatures of outlet streams in comparison to the inlet feed. An example of flashing is the removal of light hydrocarbons, dissolved gases, and a portion of the light components from a liquid mixture that includes a metal (e.g., thallium) species in solution.

Rectifying can be used to remove one or more heavier components from a vapor stream by contacting with a liquid stream. The less volatile components concentrate in the liquid stream. It is possible to contact the two streams by using a packed column, trayed column, bubble column, or centrifugal contactor. Flows can be co-current or counter-current. Rectifying can optionally be combined with chemical reactions. An example of rectifying is the removal of ester reaction products from a vapor stream by contacting with a liquid stream.

Stripping can be used to remove one or more lighter components from a liquid stream by contacting with a vapor stream. The more volatile components concentrate in the vapor stream. It is possible to contact the two streams by using a packed column, trayed column, bubble column, or centrifugal contactor. Flows can be co-current or counter-current. Vapor streams used for stripping could include steam, air, nitrogen, process streams, and/or other suitable species to achieve the desired separation. Stripping can optionally be combined with chemical reactions. An example of stripping is the removal of lighter reaction products from the liquid phase by contacting with a gas stream.

Evaporation can be used to remove lighter components by vaporization at a liquid/vapor interface. Evaporator designs may include falling film, rising film, wiped film, plate, and multi-effect evaporators. An evaporation process can optionally be combined with chemical reactions. An example of an evaporation process is the removal of acetic acid and water from a mixture of heavier liquid components, including an antimony species in solution.

Absorption (scrubbing) can be used to selectively dissolve one or more components of a gas mixture into a liquid phase. It is possible to contact the two streams by using a packed column, trayed column, bubble column, or centrifugal contactor. If a chemical reaction occurs, the process is called chemical absorption. The liquid is selected to target the desired separation. An example of absorption is the removal of water from a vapor recycle stream by contacting with a glycol mixture.

Adsorption can be used to selectively remove one or more components of a stream based on physical or chemical interactions with a solid surface. If a chemical reaction occurs, the process is called chemisorption. The solid is selected to target the desired separation. An example of adsorption is the removal of water from a liquid recycle stream using a narrow-pore silica.

Extraction (partitioning) can be used to selectively remove one or more components from a liquid phase by contacting with a second liquid phase. Due to differences in solubilities in the two liquid phases, there can be a net transfer of species from one phase to the other. An extraction process can optionally be combined with chemical reactions. An example of extraction is contacting reactor effluent with a secondary phase that selectively dissolves a specific reaction product.

Membrane separations can be used to selectively remove one or more components from a fluid stream including gases and liquids. For example, pervaporation is a process for separating one or more components from a liquid stream by partial vaporization through a porous or non-porous membrane. Vapor permeation is a process for separating one or more components from a vapor stream by utilizing a porous or non-porous membrane. The membrane materials are selected based on their different permeabilities for different components. Membrane separations can optionally be combined with chemical reactions. An example of membrane separation is the removal of water from the organic reaction mixture using a selective ceramic membrane.

The above processes can be combined to separate components of the liquid medium, for example, membrane distillation or extractive distillation.

In some embodiments, the process comprises (b) separating the oxidized intermediate and the reduced form of the oxidizing electrophile. The separating step can be by any suitable method, such as the methods described herein. For example, the oxidized intermediate and the reduced form of the oxidizing electrophile can be separated by distillation.

The present invention further encompasses a process comprising performing an elimination reaction on the oxidized intermediate to provide the alkene and re-formation of the oxygen acid. As used herein, the term "elimination reaction" refers to a class of organic chemical reactions in which a pair of atoms or groups of atoms are removed from a molecule, usually through the action of acids, bases, metals, heating (e.g., heating to a high temperature), or a combination thereof. Generally, the elimination reaction removes a hydrogen atom and a conjugate anion of the oxygen acid to produce the alkene and the corresponding oxygen acid.

In some embodiments, the elimination reaction takes place in the presence of an acid catalyst capable of facilitating the elimination reaction. As used herein, the phrase "facilitating the elimination reaction" refers to lowering the activation energy necessary for the elimination. In some embodiments, the acid catalyst is an acid (e.g., an oxygen acid), including those described herein.

In some embodiments, the elimination reaction takes place in the presence of a base catalyst capable of facilitating the elimination reaction. In some embodiments, the base catalyst is a conjugate anion of an oxygen acid described herein. In certain embodiments, a stronger base, such as an alkali metal hydroxide or alkaline earth metal hydroxide, is required to facilitate the elimination reaction.

In some embodiments, the elimination reaction occurs by heating the reaction mixture. Typically, the process of performing an elimination reaction requires higher temperatures than those required to produce the oxidized intermediate from the oxidizing electrophile and the alkane. However, in some embodiments (e.g., the elimination reaction is facilitated by an acid or a base), the elimination reaction can occur at temperatures similar to those required to produce the oxidized intermediate from the oxidizing electrophile and the alkane.

In further embodiments, the process comprises separating the alkene and the oxygen acid by any suitable method, such as those methods described herein. Preferably, the alkene and the oxygen acid are separated by distillation. In some embodiments, the separated oxygen acid is recycled for use in step (a), as described herein.

In some embodiments, the process further comprises (e) contacting the reduced form of the oxidizing electrophile and a suitable oxidizing regeneration reagent to regenerate the oxidizing electrophile. Typically, the term "oxidant" is used in the context of generating the oxidizing electrophile and the phrase "oxidizing regeneration reagent" is used in the context of regenerating the oxidizing electrophile. However, the oxidant and the oxidizing regeneration reagent can be used interchangeably, and refer to a chemical moiety used to convert the reduced form of the oxidizing electrophile to the oxidizing electrophile. The oxidizing regeneration reagent can be the same as or different from the oxidant. For example, the oxidizing regeneration reagent can be a quinone, molecular oxygen, air, ozone, a peroxide, nitric oxide, nitrous oxide, nitric acid, a nitroxide, sulfur trioxide, or a combination thereof. The peroxide can be an organic peroxide, inorganic peroxide, hydrogen peroxide, or a combination thereof In some embodiments, the oxidizing regeneration reagent can be an organic oxidant, such as a quinone or a nitroxide. In certain preferred embodiments, the oxidizing regeneration reagent is molecular oxygen, air, ozone, hydrogen peroxide, organoperoxide, nitric acid, or a combination thereof.

In some embodiments, step (e) is an electrochemical process. As used herein, an "electrochemical process" refers to a process comprising electron transfer to or from a molecule or ion using, for example, an electric current and/or an external voltage.

Thus, the process for converting an alkane to an alkene can comprise the oxidizing regeneration reagent, the oxidant, both the oxidizing regeneration reagent and the oxidant, or neither the oxidizing regeneration reagent nor the oxidant.

In some embodiments, the process for converting an alkane to an alkene comprises neither the oxidizing regeneration reagent nor the oxidant. Accordingly, the oxidizing regeneration reagent and the oxidant can be present in an amount of 0 mol % (e.g., below the level of detection) of the main group element.

In some embodiments, the oxidizing regeneration reagent and/or the oxidant are present in the liquid medium. The amount of the oxidizing regeneration reagent and/or the oxidant is not particularly limited, so long as a sufficient amount of the oxidizing electrophile is maintained in the liquid medium to convert a portion of the alkane to an alkene. Accordingly, the oxidizing regeneration reagent and/or the oxidant can be present in an amount of about 0.1 mol % of the alkane or more (e.g., about 0.2 mol % or more, about 0.3 mol % or more, about 0.4 mol % or more, about 0.5 mol % or more, about 1 mol % or more, about 2 mol % or more, about 3 mol % or more, about 5 mol % or more, about 10 mol % or more, about 20 mol % or more, about 50 mol % or more, or about 100 mol % or more). Alternatively, or in addition, the oxidizing regeneration reagent and/or the oxidant can be present in an amount of about 2000 mol % of the alkane or less (e.g., about 1500 mol % or less, about 1000 mol % or less, about 900 mol % or less, about 800 mol % or less, about 700 mol % or less, about 600 mol % or less, about 500 mol % or less, about 400 mol % or less, about 300 mol % or less, about 200 mol % or less, or about 100 mol % or less). Any two of the foregoing endpoints can be used to define a close-ended range, or any single endpoint can be used alone to define an open-ended range.

In some embodiments, the reduced form of the oxidizing electrophile and the oxidizing regeneration reagent are contacted to regenerate the oxidizing electrophile in the presence of an oxidative regeneration catalyst. The oxidative regeneration catalyst can be any suitable catalyst, such as an oxidative regeneration catalyst that comprises copper, silver, iron, cobalt, manganese, nickel, chromium, vanadium, or a combination thereof.

In certain embodiments, the oxidizing regeneration reagent oxidizes the reduced form of the oxidizing electrophile to the oxidizing electrophile in the liquid medium in the presence of the alkane. In certain embodiments, the oxidizing regeneration reagent oxidizes the reduced form of the oxidizing electrophile to the oxidizing electrophile in a separate reactor, and is added back to the liquid medium. Accordingly, the regenerated oxidizing electrophile can be recycled for use in step (a), as described herein.

The process for converting an alkane to an alkene can further comprise recycling any of the components, that are not consumed in the process, to be reused in the process (e.g., recycling to be reused in the liquid medium and/or the oxidizing composition). For example, the substrate, oxidizing electrophile, non-oxidizable liquid, additive, or any combination thereof can be recycled and reused in the process.

In some embodiments, the process for converting an alkane to an alkene comprises the oxidizing electrophile and/or the reduced form of an oxidizing electrophile, and liquid medium as a heterogeneous mixture or a homogenous mixture.

As used herein, the phrase "homogeneous mixture" refers to a uniform composition containing one or more phases, e.g., liquid/liquid, liquid/solid, liquid/gas, solid/gas, or liquid/solid/gas. Thus, a homogeneous mixture comprising a liquid can also contain a gas and/or a solid, only if the gas and/or the solid is soluble in the liquid as to form a uniform composition. In embodiments where the liquid medium is a homogeneous mixture, the oxidizing electrophile and/or the reduced form of an oxidizing electrophile are soluble in the liquid medium.

In preferred embodiments, the liquid medium is a homogeneous mixture. In other preferred embodiments, the liquid medium is a heterogeneous mixture, wherein any component can be insoluble in the liquid medium, as long as the oxidizing electrophile maintains a certain level of solubility. Without wishing to be bound by any particular theory, it is believed that the reaction is more efficient when at least the oxidizing electrophile is soluble in the liquid medium. In some embodiments, the liquid medium can transition from a homogeneous mixture to a heterogeneous mixture and from a heterogeneous mixture to a homogeneous mixture.

In some embodiments, the oxidizing electrophile maintains a level of solubility such that about 25% or less of the total mass of the oxidizing electrophile is an insoluble solid in the mixture (e.g., about 20% or less, about 15% or less, about 12% or less, about 10% or less, about 5% or less, or about 1% or less). Alternatively, the oxidizing electrophile can be completely soluble in the liquid medium (e.g., about 0% of the total mass of the oxidizing electrophile is an insoluble solid in the mixture). Thus, the oxidizing electrophile maintains a level of solubility such that about 0% to about 25% of the total mass of the oxidizing electrophile is an insoluble solid in the mixture (e.g., about 0% to about 20%, about 0% to about 15%, about 0% to about 12%, about 0% to about 10%, about 0% to about 5%, or about 0% to about 1%).

As used herein, the phrase "insoluble solid" refers to any solid that does not readily dissolve in the liquid medium as to form a uniform (e.g., homogeneous) composition. The amount of insoluble solid can be determined by any suitable means. For example, the amount of insoluble solid can be filtered from the liquid medium using microfiltration (i.e., filters ranging from about 0.1 microns to about 1.0 micron). Accordingly, the percentage of total mass of the oxidizing electrophile that exists as an insoluble solid in the mixture can be determined by the mass of insoluble oxidizing electrophile filtered from the liquid medium using microfiltration divided by the theoretical total mass of the oxidizing electrophile in the mixture.

In some embodiments, regardless of whether the mixture is heterogeneous or homogeneous, the reduced form and oxidized form of the electrophile comprising the main group element are soluble in the liquid medium. Accordingly, the mixture is substantially free (e.g., about 0 mass % and/or below the level of detection) of a solid comprising the oxidizing electrophile.

The process for converting an alkane to an alkene can be carried out in a single reactor or carried out in at least 2 reactors (e.g., at least 3 or at least 4 reactors). When the process is carried out in a single reactor and the oxidizing electrophile is present in at least a stoichiometric quantity, the process for converting an alkane to an alkene does not necessitate regeneration of the oxidizing electrophile. In this embodiment, the process for converting an alkane to an alkene can be carried out under a single set of conditions in the single reactor.

Alternatively, the process can be carried out in a single reactor, in which the reactor is operated under conditions suitable for converting the alkane to the alkene using the oxidizing electrophile and simultaneous regeneration of the oxidizing electrophile by contacting the electrophile reduction product and the oxidizing regeneration reagent. For example, when the oxidizing electrophile is depleted, the oxidizing regeneration reagent, optionally in the presence of an oxidative regeneration catalyst, is present in the liquid medium to regenerate the oxidizing electrophile.

In some embodiments, the process can be carried out in a single reactor in a sequential manner. For example, the reactor can be operated first under conditions suitable for converting the alkane to the oxidized intermediate using the oxidizing electrophile and then performing the elimination reaction, then subsequently operated under conditions suitable for regeneration of the oxidizing electrophile by contacting the electrophile reduction product and the oxidizing regeneration reagent. For example, the oxidizing electrophile can be immobilized within the reactor, in which first a mixture comprising the alkane is circulated, then, when the oxidizing electrophile is depleted and/or the alkene is isolated, a mixture comprising the oxidizing regeneration reagent, optionally in the presence of an oxidative regeneration catalyst, is circulated to regenerate the oxidizing electrophile.

Alternatively, the process can be carried out in a two reactor circulating liquid phase system, in which the reaction of the alkane to the alkene is carried out in a first reactor, and the reaction of the electrophile reduction product and the oxidizing regeneration reagent used to regenerate the oxidizing electrophile is carried out in a second reactor.

Alternatively, the process can be carried out in a three reactor circulating liquid phase system, in which the reaction of the alkane to the oxidized intermediate is carried out in a first reactor, the elimination reaction of the oxidized intermediate to the alkene is carried out in a second reactor, and the reaction of the electrophile reduction product and the oxidizing regeneration reagent used to regenerate the oxidizing electrophile is carried out in a third reactor.

The process of the present invention can take place at any temperature suitable for forming an oxidized intermediate, and ultimately, forming an alkene. In some embodiments, the process for oxidizing an alkane can be performed at less than about 300° C., for example, less than about 285° C., less than about 275° C., less than about 260° C., less than about 250° C., less than about 225° C., less than about 200° C., less than about 150° C., or less than about 140° C. Alternatively, or in addition to, the process for oxidizing an alkane can be performed at greater than about 50° C., for example, greater than about 70° C., greater than about 80° C., greater than about 100° C., greater than about 120° C., greater than about 140° C., greater than about 150° C., greater than about 160° C., greater than about 170° C., greater than about 180° C., greater than about 190° C., or greater than about 200° C. Any two of the foregoing endpoints can be used to define a close-ended range, or one endpoint can be used alone to define an open-ended range. Thus, the process can be performed at a temperature between about 50° C. to about 300° C., for example, about 50° C. to about to about 275° C., about 50° C. to about 250° C., about 50° C. to about 225° C., about 50° C. to about 200° C., about 70° C. to about 200° C., about 80° C. to about 200° C., about 70° C. to about 140° C., about 100° C. to about 200° C., about 120° C. to about 200° C., about 140° C. to about 200° C., about 150° C. to about 200° C., about 160° C. to about 200° C., about 170° C. to about 200° C., about 180° C. to about 200° C., about 190° C. to about 200° C., about 200° C. to about 300° C., about 200° C. to about 350° C., about 100° C. to about 300° C., or about 150° C. to about 250° C. In some embodiments, the temperature is between about 50° C. to about 300° C., and more preferably, between about 70° C. to about 140° C.

The process of the present invention can take place at any pressure suitable for forming an oxidized intermediate, and ultimately, forming an alkene. In some embodiments, the process for oxidizing an alkane can be performed at less than about 2000 psi (about 13800 kPa), for example, less than about 1500 psi (about 10300 kPa), less than about 1000 psi (about 6900 kPa), less than about 500 psi (about 3450 kPa), less than about 400 psi (about 2800 kPa), less than about 300 psi (about 2100 kPa), or less than about 200 psi (about 1400 kPa). Alternatively, or in addition to, the process for oxidizing an alkane can be performed at greater than about 0 psi (about 0 kPa), for example, greater than about 1 psi (about 6.9 kPa), greater than about 2 psi (about 13.8 kPa), greater than about 3 psi (about 20.7 kPa), greater than about 4 psi (about 27.6 kPa), greater than about 5 psi (about 34.5 kPa), greater than about 10 psi (about 69 kPa), or greater than about 20 psi (about 138 kPa). Any two of the foregoing endpoints can be used to define a close-ended range, or one endpoint can be used alone to define an open-ended range. Thus, the process can be performed at a pressure between about 0 psi (about 0 kPa) to about 2000 psi (about 13800 kPa), for example, about 0 psi (about 0 kPa) and about 1500 psi (about 10300 kPa), about 0 psi (about 0 kPa) and about 1000 psi (about 6900 kPa), about 0 psi (about 0 kPa) and about 500 psi (about 3450 kPa), about 0 psi (about 0 kPa) and about 400 psi (about 2800 kPa), about 0 psi (about 0 kPa) and about 300 psi (about 2100 kPa), about 0 psi (about 0 kPa) and about 200 psi (about 1400 kPa), about 2 psi (about 13.8 kPa) and about 1500 psi (about 10300 kPa), about 2 psi (about 13.8 kPa) and about 1000 psi (about 6900 kPa), about 2 psi (about 13.8 kPa) and about 500 psi (about 3450 kPa), about 2 psi (about 13.8 kPa) and about 400 psi (about 2800 kPa), about 2 psi (about 13.8 kPa) and about 300 psi (about 2100 kPa), about 2 psi (about 13.8 kPa) and about 200 psi (about 1400 kPa), about 5 psi (about 34.5 kPa) and about 1500 psi (about 10300 kPa), about 5 psi (about 34.5 kPa) and about 1000 psi (about 6900 kPa), about 5 psi (about 34.5 kPa) and about 500 psi (about 3450 kPa), about 5 psi (about 34.5 kPa) and about 400 psi (about 2800 kPa), about 5 psi (about 34.5 kPa) and about 300 psi (about 2100 kPa), or about 5 psi (about 34.5 kPa) and about 200 psi (about 1400 kPa), In some embodiments, the pressure is between about 2 psi (about 13.8 kPa) and about 500 psi (about 3450 kPa), and more preferably, between about 5 psi (about 34.5 kPa) and about 200 psi (about 1400 kPa).

The invention is further illustrated by the following embodiments.

(1) A process for converting an alkane to an alkene, comprising (a) contacting the alkane and (i) an oxidizing electrophile comprising a main group element in oxidized form or (ii) an oxidant and a reduced form of the oxidizing electrophile, in a liquid medium comprising an oxygen acid and optionally one or more additives selected from a non-oxidizable liquid, a salt additive, a Lewis acid, and water, to provide an oxidized intermediate and a reduced form of the oxidizing electrophile; (b) optionally separating the oxidized intermediate and the reduced form of the oxidizing electrophile; and (c) performing an elimination reaction on the oxidized intermediate to provide the alkene and the oxygen acid.

(2) The process of embodiment (1), comprising (b) separating the oxidized intermediate and the reduced form of the oxidizing electrophile.

(3) The process of embodiment (1) or embodiment (2), wherein (c) takes place in the presence of an acid catalyst.

(4) The process of embodiment (1) or embodiment (2), wherein (c) takes place in the presence of a base catalyst.

(5) The process of any one of embodiments (1)-(4), further comprising (d) separating the alkene and the oxygen acid.

(6) The process of embodiment (5), wherein the separated oxygen acid is recycled for use in step (a).

(7) The process of any one of embodiments (1)-(6), wherein the alkane is a $C_2$-$C_{20}$ alkane, a $C_2$-$C_{20}$ heteroalkane, $C_3$-$C_{20}$ cycloalkane, $C_3$-$C_{20}$ heterocycloalkane, arylalkane, heteroarylalkane, or a combination thereof.

(8) The process of embodiment (7), wherein the alkane is ethane, propane, butane, or a mixture thereof.

(9) The process of any one of embodiments (1)-(8), wherein the oxidizing electrophile comprises a main group element.

(10) The process of embodiment (9), wherein the oxidizing electrophile comprises gallium, germanium, arsenic, tin, thallium, lead, antimony, selenium, tellurium, bismuth, or iodine.

(11) The process of embodiment (10), wherein the oxidizing electrophile comprises Sb(V), Te(VI), Te(IV), Bi(V), Se(VI), Se(IV), As(V), I(V), I(III), or Sn(IV).

(12) The process of any one of embodiments (1)-(11), wherein the oxidizing electrophile comprises at least one conjugate anion of an oxygen acid.

(13) The process of embodiment (12), wherein the conjugate anion of the oxygen acid is an aliphatic carboxylate, heteroaliphatic carboxylate, aromatic carboxylate, heteroaromatic carboxylate, aliphatic sulfonate, heteroaliphatic sulfonate, aromatic sulfonate, heteroaromatic sulfonate, aliphatic phosphate, heteroaliphatic phosphate, aromatic phosphate, heteroaromatic phosphate, aliphatic borate, heteroaliphatic borate, aromatic borate, heteroaromatic borate, or a mixture thereof

(14) The process of embodiment (13), wherein the conjugate anion of the oxygen acid is trifluoroacetate, acetate, alkylsulfonate, phosphate, nitrate, sulfate, trifluoromethanesulfate, or fluorosulfate.

(15) The process of any one of embodiments (1-14), wherein the oxidizing electrophile has a formula $M^{+n}X_pL_q$, wherein M is a main group element cation in an oxidation state of n, X is the conjugate anion of the oxygen acid, L is a ligand, n is an integer from 2 to 6, p is an integer from 1 to 6, and q is an integer from 0 to 5.

(16) The process of embodiment (15), wherein $M^{+n}X_pL_q$ undergoes reaction with the alkane in the liquid medium to yield a reduced form of the oxidizing electrophile of formula $M^{+(n-2)}X_{p-2}L_q$ or $M^{+(n-1)}X_{p-1}L_q$.

(17) The process of any one of embodiments (1)-(16), wherein the oxidizing electrophile is present in at least stoichiometric quantities relative to the amount of alkene produced.

(18) The process of any one of embodiments (1)-(17), wherein the oxidizing electrophile is present in less than stoichiometric quantities relative to the alkane and acts as a catalyst.

(19) The process of embodiment (18), further comprising (e) contacting the reduced form of the oxidizing electrophile and an oxidizing regeneration reagent to regenerate the oxidizing electrophile.

(20) The process of embodiment (19), wherein the oxidizing regeneration reagent is a quinone, molecular oxygen, air, ozone, a peroxide, nitric oxide, nitrous oxide, nitric acid, a nitroxide, sulfur trioxide, or a combination thereof.

(21) The process of embodiment (19), wherein step (e) is an electrochemical process.

(22) The process of any one of embodiments (19)-(21), wherein the reduced form of the oxidizing electrophile and the oxidizing regeneration reagent are contacted to regenerate the oxidizing electrophile in the presence of an oxidative regeneration catalyst.

(23) The process of embodiment (22), wherein the oxidative regeneration catalyst comprises copper, silver, iron, cobalt, manganese, nickel, chromium, vanadium, or a combination thereof.

(24) The process of any one of embodiments (19)-(23), wherein the oxidizing regeneration reagent oxidizes the reduced form of the oxidizing electrophile to the oxidizing electrophile in the liquid medium in the presence of the alkane.

(25) The process of any one of embodiments (19)-(24), wherein the regenerated oxidizing electrophile is recycled for use in step (a).

(26) The process of any one of embodiments (1)-(25), wherein the oxygen acid is aliphatic carboxylic acid, heteroaliphatic carboxylic acid, aromatic carboxylic acid, heteroaromatic carboxylic acid, aliphatic sulfonic acid, heteroaliphatic sulfonic acid, aromatic sulfonic acid, heteroaromatic sulfonic acid, aliphatic phosphonic acid, heteroaliphatic phosphonic acid, aromatic phosphonic acid, heteroaromatic phosphonic acid, boric acid, aliphatic boronic acid, heteroaliphatic boronic acid, aromatic boronic acid, heteroaromatic boronic acid, or a mixture thereof.

(27) The process of any one of embodiments (1)-(26), wherein the oxygen acid is trifluoroacetic acid, acetic acid, methanesulfonic acid, phosphoric acid, nitric acid, sulfuric acid, trifluoromethanesulfonic acid, fluorosulfuric acid, or a mixture thereof.

(28) The process of any of embodiments (1)-(27), wherein all or a portion of the oxygen acid is added as an anhydride of the oxygen acid.

(29) The process of any one of embodiments (1)-(28), wherein the liquid medium comprises a non-oxidizable liquid selected from a fluorinated hydrocarbon, a sulfone, a deactivated arene, a deactivated aliphatic, a deactivated heteroarene, a deactivated heteroaliphatic, or a combination thereof, wherein the liquid is substantially inert in the presence of the oxidizing electrophile.

(30) The process of any one of embodiments (1)-(29), wherein the liquid medium comprises a salt additive.

(31) The process of embodiment (30), wherein the liquid medium comprises a salt additive of formula $Q_aZ_b$, wherein Q is a cation, Z is a bridging oxide, a terminal oxide, a hydroxide, or a conjugate anion of an oxygen acid, a is an integer from 1 to 5, and b is an integer from 1 to 5, wherein a and b are the same or different and balance the oxidation states of Q and Z.

(32) The process of embodiment (31), wherein Z is a conjugate anion of an oxygen acid that is one or more selected from an aliphatic carboxylate, heteroaliphatic carboxylate, aromatic carboxylate, heteroaromatic carboxylate, aliphatic sulfonate, heteroaliphatic sulfonate, aromatic sulfonate, heteroaromatic sulfonate, aliphatic phosphate, heteroaliphatic phosphate, aromatic phosphate, heteroaromatic phosphate, aliphatic borate, heteroaliphatic borate, aromatic borate, heteroaromatic borate, or a mixture thereof.

(33) The process of embodiment (31) or (32), wherein Q is a proton, a cation of an alkali metal, a cation of an alkaline earth metal, a cation of a rare-earth metal, a main group element cation, or a combination thereof.

(34) The process of any one of embodiment (1)-(33), wherein the liquid medium comprises a Lewis acid.

(35) The process of any one of embodiments (1)-(34), wherein the reaction temperature in (a) is from about 50° C. to about 300° C.

(36) The process of any one of embodiments (1)-(35), wherein the reaction pressure in (a) is between about 2 psi (about 13.8 kPa) and about 500 psi (about 3450 kPa).

The following examples further illustrate the invention but, of course, should not be construed as in any way limiting its scope.

EXAMPLE 1

Figure 3:
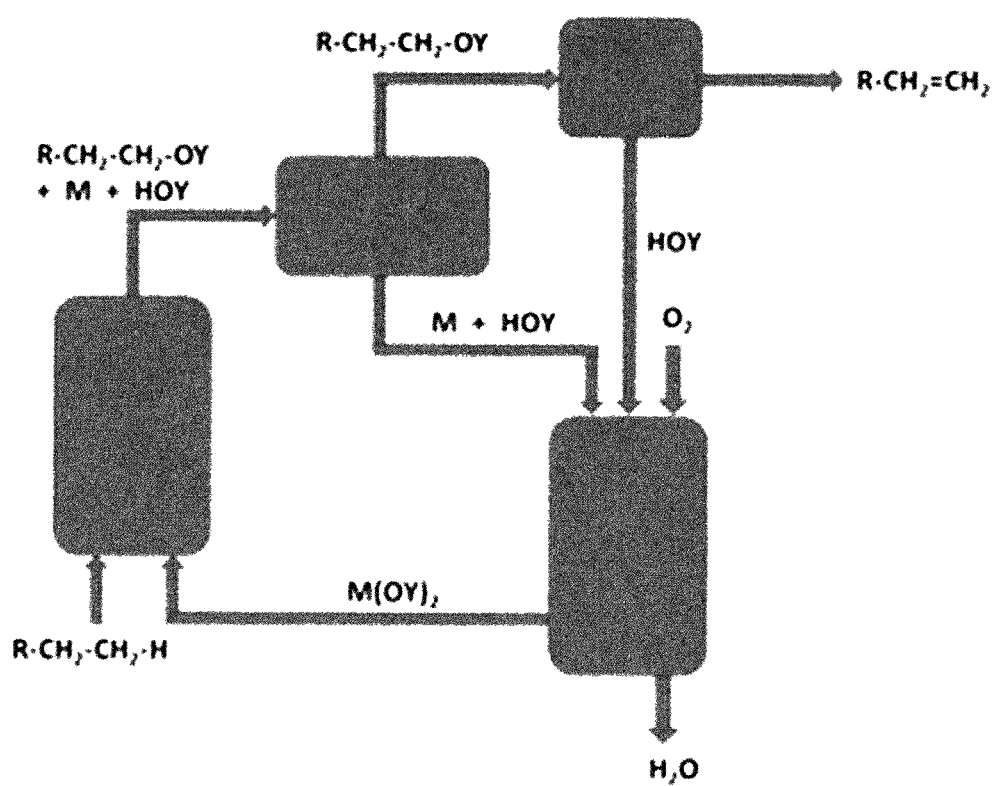
FIG. 3 illustrates an exemplary reaction cycle for the oxidation process, which includes separation of the oxidized intermediate.

This example demonstrates proposed process steps for the conversion of an alkane (R—$CH_2$—$CH_2$—H) to an alkene (R—CH=$CH_2$) in a reactor. The process includes separating the oxidized intermediate (R—$CH_2$—$CH_2$—OY) and the reduced form of the oxidizing electrophile (M). FIG. 3 is a schematic depicting this process.

The process involves the generation of an oxidizing electrophile ($M(OY)_2$) that reacts with the alkane to generate the oxidized intermediate, the reduced form of the oxidizing electrophile, and an oxygen acid (HOY). Here, M is the reduced form of the oxidizing electrophile, OY is the conjugate anion of the oxygen acid. The OY group allows for the generation of an electrophilic M-center in $M(OY)_2$ species and protects the oxidized intermediate from further electrophilic reactions.

Separation of the oxidized intermediate from the reduced form of the oxidizing electrophile, and the oxygen acid, followed by elimination yields the desired alkene. The elimination step can occur at elevated temperatures and/or be facilitated by a catalyst (e.g., an acid or a base). An integral part of this process involves the elimination of the alkyl ester in a separate step from the formation of the oxidized intermediate.

The oxidizing electrophilic M-center (M) can be regenerated from $O_2$, or other suitable oxidants, in the presence of the acid (HOY) to yield the oxidized electrophilic M-center ($M(OY)_2$). Although this process is demonstrated on the primary carbon, this reaction can occur on any alkane where two adjacent carbons each have a hydrogen atom.

As shown in FIG. 3, this process can be a "closed loop" in which the desired alkene is removed from the reactor, and the oxidizing electrophile is regenerated to begin the process again.

EXAMPLE 2

Figure 4:
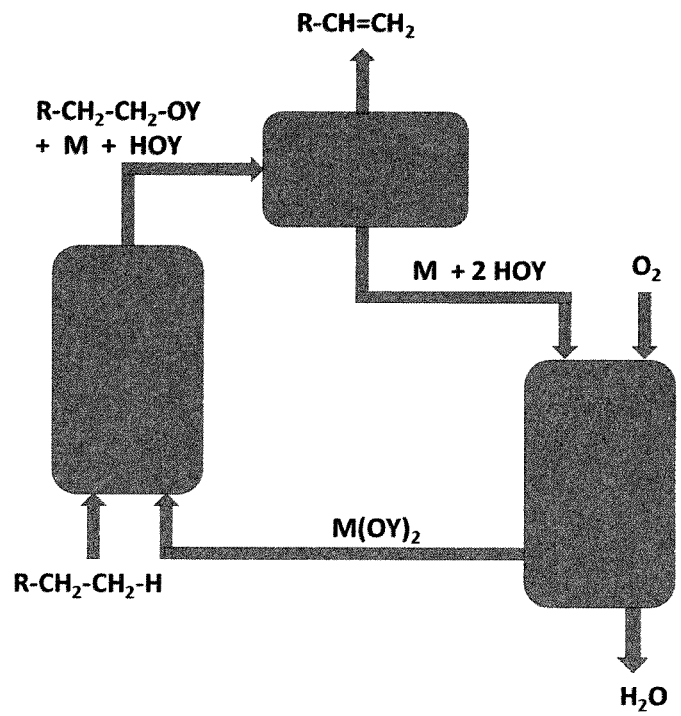
FIG. 4 illustrates an exemplary reaction cycle for the oxidation process, which does not include separation of the oxidized intermediate.

This example demonstrates alternative process steps for the conversion of alkanes (R—$CH_2$—$CH_2$—H) to alkenes (R—CH=$CH_2$) in a reactor. The following steps can be performed in such cases where the oxidized intermediate (R—$CH_2$—$CH_2$—OY) is inseparable from the reaction mixture (e.g., the oxidized intermediate is not a distillable product or has a higher boiling point than the non-oxidizable liquid). FIG. 4 is a schematic depicting this process.

The process involves the generation of an oxidizing electrophile ($M(OY)_2$) that reacts with the alkane to generate the oxidized intermediate, the reduced form of the oxidizing electrophile, and an oxygen acid (HOY). Here, M is the reduced form of the oxidizing electrophile, and OY is the conjugate anion of the oxygen acid. The OY group allows for the generation of an electrophilic M-center in the $M(OY)_2$ species and protects the oxidized intermediate from further electrophilic reactions.

Upon completion of the oxidation step, elimination of the conjugate anion of the oxygen acid from the oxidized intermediate yields the desired alkene, which can be separated from the reaction mixture. The elimination step can occur at elevated temperatures and/or be facilitated by a catalyst (e.g., an acid or a base). An integral part of this process involves the elimination of the alkyl ester in the same reactor as the one in which the formation of the oxidized intermediate occurs. Exemplary oxidized intermediates that can require the oxidized intermediate to not be separated include aryl esters, sulfonic esters, and other high boiling point esters. In these steps, the elimination reaction is performed in the presence of the reduced form of the oxidant (M).

Such a system would require very high conversion of $M(OY)_2$ to M. If not, it is possible that the resulting alkene would react with the residual oxidizing electrophile to yield the corresponding glycol.

The oxidized electrophilic M-center (M) can be regenerated from $O_2$, or other suitable oxidants, in the presence of the acid (HOY) to yield the oxidized electrophilic M-center ($M(OY)_2$). Although this process is demonstrated on the primary carbon, this reaction can occur on any alkane where two adjacent carbons each have a hydrogen atom.

As shown in FIG. 4, this process can be a "closed loop" in which the desired alkene is removed from the reactor, and the oxidizing electrophile is regenerated to begin the process again.

EXAMPLE 3

Figure 5:
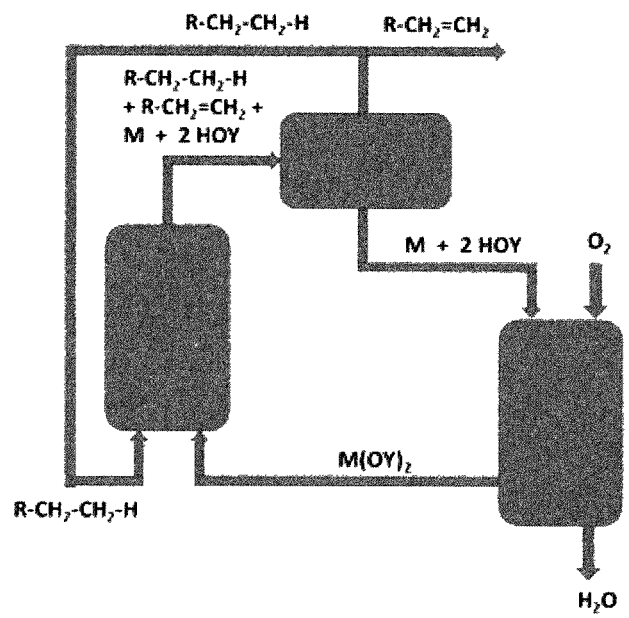
FIG. 5 illustrates an exemplary reaction cycle for the oxidation process in a single pot.

This example demonstrates alternative process steps for the conversion of alkanes (R—$CH_2$—$CH_2$—H) to alkenes (R—CH=$CH_2$) in a single pot. The process includes formation of the oxidized intermediate (R—$CH_2$—$CH_2$—OY) and the alkene concurrently. FIG. 5 is a schematic depicting this process.

The process involves the generation of an oxidizing electrophile ("M(OY)$_2$") that reacts with the alkane to generate the oxidized intermediate, the reduced form of the oxidizing electrophile, and an oxygen acid ("HOY"). Here, M is the reduced form of the oxidizing electrophile, and OY is the conjugate anion of the oxygen acid. The OY group allows for the generation of an electrophilic M-center in M(OY)$_2$ species and protects the oxidized intermediate from further electrophilic reactions.

Elimination of the conjugate anion of the oxygen acid from the oxidized intermediate yields the desired alkene, which can be separated from the reaction mixture. The elimination step can occur at elevated temperatures and/or be facilitated by a catalyst (e.g., an acid or a base). An integral part of this process involves the elimination of the alkyl ester in the same reactor as the one in which the formation of the oxidized intermediate occurs. Exemplary oxidized intermediates that can require the oxidized intermediate to not be separated include aryl esters, sulfonic esters, and other high boiling point esters. In these steps, the elimination reaction is performed in the presence of the reduced form of the oxidant (M).

The one pot procedure can be a streamlined approached to produce the alkene in a single reactor. However, the one pot approach can result in product mixtures stemming from the oxidation of the alkene product. Such mixtures can be tempered by removal of the alkene upon formation. Removal of the alkene can result in concurrent removal of the alkane, which can be recycled back into the reaction mixture (FIG. 5).

The oxidized electrophilic M-center (M) can be regenerated from $O_2$, or other suitable oxidants, in the presence of the acid (HOY) to yield the oxidized electrophilic M-center (M(OY)$_2$). Although this process is demonstrated on the primary carbon, this reaction can occur on any alkane where two adjacent carbons each have a hydrogen atom.

As shown in FIG. 5, this process can be a "closed loop" in which the desired alkene is removed from the reactor, and the oxidizing electrophile is regenerated to begin the process again.

EXAMPLE 4

This example demonstrates the oxidation of an alkane to an alkene in the presence of an oxidation composition containing a non-oxidizable liquid, an oxidizing electrophile, and optionally an additive.

The substrate (e.g., ethyl benzene, pentyl trifluoroacetate, and ethyl pyridine) was dissolved in the corresponding non-oxidizable liquid (liquid species) to yield a 0.5 M solution. The oxidizing electrophile (e.g., Tl(X)$_3$, Pb(X)$_4$, $C_6F_5I(X)_2$, Sb(X)$_3$ and $H_2O_2$, Te(X)$_6$, and Hg(X)$_2$) was dissolved in the corresponding liquid species to yield a 0.2 M solution. "X" is as defined in FIG. 6A. 2.0 mL of the oxidant solution was added to a 2-5 ml microwave vial equipped with a stir bar. The substrate solution (2.0 mL) was added to the microwave vial. The additives (if present) were added to the reaction and the crimp seal cap was sealed to the top of the vial. For gaseous substrates (e.g., propane, and ethane), the reaction vial was charged with the gaseous substrate prior to sealing.

For the preparation of the Sb(TFA)$_3$ and $H_2O_2$ solution, the following procedure was followed. Sb(TFA)$_3$ and additives (except anhydrides) were dissolved in trifluoroacetic acid (TFAH) (10% less than total theoretical volume) in a vial and the solution was cooled with an ice bath. The 50% $H_2O_2$ in $H_2O$ was added to the solution and stirred for 10 min. The anhydride was added, the vial was capped, and stirred for 10 min at room temperature. The solution was opened and TFAH was added to achieve desired final volume to give the correct Sb concentration.

The vials were placed into a preheated aluminum block set to the appropriate temperature (100-200° C.). The reactions were stirred at temperature for 1 h. The vials were removed from the heat and cooled to room temperature. 1.0 ml of the solutions were added to a 1-dram vial and a standard was added to the solution. A sample of the solution was added to an NMR tube equipped with a capillary containing $d_6$-benzene. Quantitative NMR spectra were acquired for each sample. The results are set forth in FIG. 6B.

The resulting oxidized intermediates can be heated in a solvent (e.g., dimethyl sulfone) to afford the corresponding alkenes in yields approaching stoichiometric conversion.

As is apparent from the results set forth in in FIG. 6B, the non-oxidizable liquids (liquid species) are not only stable to the reaction conditions, but also produce oxidizing compositions capable of oxidizing an alkane to an oxidized intermediate. The resulting oxidized intermediate can be readily converted to an alkene by heating.

EXAMPLE 5

This example demonstrates the oxidation of an alkane to an alkene in a single pot with a non-oxidizable liquid, an oxidizing electrophile, and optionally an additive.

Na[Sb(OMs)$_6$] was dissolved in a preheated solution of dimethylsulfone (DMS). The solution was exposed to 125 psi of propane in a SS reactor for 3 h at 195° C. The gas phase was vented into a solution of $H_2SO_4$ with an AcOH standard. The captured product was shown to be iPrOH (7% yield based on Sb(V)). Test reactions showed that heating iPrOMs in a solution of DMS gives a clean conversion to propylene under reaction conditions.

Thus, the oxidized intermediate formed from oxidation with a non-oxidizable liquid, an oxidizing electrophile, and optionally an additive can be readily converted to the corresponding alkene upon heating.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments can become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A process for converting an alkane to an alkene, comprising
   (a) contacting the alkane and
   (i) an oxidizing electrophile comprising a main group element selected from gallium, germanium, arsenic, tin, thallium, lead, antimony, bismuth, and iodine, each in oxidized form or
   (ii) an oxidant and a reduced form of the oxidizing electrophile,
   in a liquid medium comprising an oxygen acid and optionally one or more additives selected from a non-oxidizable liquid, a salt additive, a Lewis acid, and water, to provide an oxidized intermediate and a reduced form of the oxidizing electrophile;
   (b) optionally separating the oxidized intermediate and the reduced form of the oxidizing electrophile; and
   (c) performing an elimination reaction on the oxidized intermediate to provide the alkene and the oxygen acid.

2. The process of claim 1, comprising (b) separating the oxidized intermediate and the reduced form of the oxidizing electrophile.

3. The process of claim 1, wherein (c) takes place in the presence of an acid catalyst.

4. The process of claim 1, wherein (c) takes place in the presence of a base catalyst.

5. The process of claim 1, further comprising (d) separating the alkene and the oxygen acid.

6. The process of claim 5, wherein the separated oxygen acid is recycled for use in step (a).

7. The process of claim 1, wherein the oxidizing electrophile comprises arsenic, antimony, or bismuth.

8. The process of claim 1, wherein the oxidizing electrophile comprises at least one conjugate anion of an oxygen acid.

9. The process of claim 8, wherein the conjugate anion of the oxygen acid is an aliphatic carboxylate, heteroaliphatic carboxylate, aromatic carboxylate, heteroaromatic carboxylate, aliphatic sulfonate, heteroaliphatic sulfonate, aromatic sulfonate, heteroaromatic sulfonate, aliphatic phosphate, heteroaliphatic phosphate, aromatic phosphate, heteroaromatic phosphate, aliphatic borate, heteroaliphatic borate, aromatic borate, heteroaromatic borate, or a mixture thereof.

10. The process of claim 1, wherein the oxidizing electrophile has a formula $M^{+n}X_pL_q$, wherein M is a main group element cation in an oxidation state of n, X is the conjugate anion of the oxygen acid, L is a ligand, n is an integer from 2 to 6, p is an integer from 1 to 6, and q is an integer from 0 to 5.

11. The process of claim 1, wherein the oxidizing electrophile is present in less than stoichiometric quantities relative to the alkane and acts as a catalyst.

12. The process of claim 11, further comprising (e) contacting the reduced form of the oxidizing electrophile and an oxidizing regeneration reagent to regenerate the oxidizing electrophile.

13. The process of claim 12, wherein the oxidizing regeneration reagent is a quinone, molecular oxygen, air, ozone, a peroxide, nitric oxide, nitrous oxide, nitric acid, a nitroxide, sulfur trioxide, or a combination thereof.

14. The process of claim 12, wherein step (e) is an electrochemical process.

15. The process of claim 12, wherein the reduced form of the oxidizing electrophile and the oxidizing regeneration reagent are contacted to regenerate the oxidizing electrophile in the presence of an oxidative regeneration catalyst.

16. The process of claim 15, wherein the oxidative regeneration catalyst comprises copper, silver, iron, cobalt, manganese, nickel, chromium, vanadium, or a combination thereof.

17. The process of claim 1, wherein the oxygen acid is aliphatic carboxylic acid, heteroaliphatic carboxylic acid, aromatic carboxylic acid, heteroaromatic carboxylic acid, aliphatic sulfonic acid, heteroaliphatic sulfonic acid, aromatic sulfonic acid, heteroaromatic sulfonic acid, aliphatic phosphonic acid, heteroaliphatic phosphonic acid, aromatic phosphonic acid, heteroaromatic phosphonic acid, boric acid, aliphatic boronic acid, heteroaliphatic boronic acid, aromatic boronic acid, heteroaromatic boronic acid, or a mixture thereof.

18. The process of claim 1, wherein all or a portion of the oxygen acid is added as an anhydride of the oxygen acid.

19. The process of claim 1, wherein the liquid medium comprises a non-oxidizable liquid selected from a fluorinated hydrocarbon, a sulfone, a deactivated arene, a deactivated aliphatic, a deactivated heteroarene, a deactivated heteroaliphatic, or a combination thereof, wherein the liquid is substantially inert in the presence of the oxidizing electrophile.

20. The process of claim 1, wherein the liquid medium comprises a salt additive.

21. The process of claim 20, wherein the liquid medium comprises a salt additive of formula $Q_aZ_b$, wherein Q is a cation, Z is a bridging oxide, a terminal oxide, a hydroxide, or a conjugate anion of an oxygen acid, a is an integer from 1 to 5, and b is an integer from 1 to 5, wherein a and b are the same or different and balance the oxidation states of Q and Z.

22. The process of claim 21, wherein Z is a conjugate anion of an oxygen acid that is one or more selected from an aliphatic carboxylate, heteroaliphatic carboxylate, aromatic carboxylate, heteroaromatic carboxylate, aliphatic sulfonate, heteroaliphatic sulfonate, aromatic sulfonate, heteroaromatic sulfonate, aliphatic phosphate, heteroaliphatic phosphate, aromatic phosphate, heteroaromatic phosphate, aliphatic borate, heteroaliphatic borate, aromatic borate, heteroaromatic borate, and a mixture thereof.

23. The process of claim 1, wherein the liquid medium comprises a Lewis acid.

* * * * *